US012678062B2

(12) United States Patent
Moon et al.

(10) Patent No.: US 12,678,062 B2
(45) Date of Patent: Jul. 14, 2026

(54) DISPLAY DEVICE AND BLOOD PRESSURE MEASUREMENT METHOD USING THE SAME

(71) Applicant: SAMSUNG DISPLAY CO., LTD., Yongin-si (KR)

(72) Inventors: Gyeong Ub Moon, Suwon-si (KR); Bo Ram Choi, Asan-si (KR); Jong Yeop An, Hwaseong-si (KR); Hyeon Jun Lee, Hanam-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 889 days.

(21) Appl. No.: 17/965,159

(22) Filed: Oct. 13, 2022

(65) Prior Publication Data

US 2023/0320597 A1 Oct. 12, 2023

(30) Foreign Application Priority Data

Mar. 24, 2022 (KR) ........................ 10-2022-0036657

(51) Int. Cl.
*A61B 5/021* (2006.01)
*A61B 5/00* (2006.01)
*A61B 5/024* (2006.01)

(52) U.S. Cl.
CPC ...... *A61B 5/02116* (2013.01); *A61B 5/02416* (2013.01); *A61B 5/6897* (2013.01);
(Continued)

(58) Field of Classification Search
CPC . A61B 5/021; A61B 5/02108; A61B 5/02116; A61B 5/0225; A61B 5/02416;
(Continued)

(56) References Cited

U.S. PATENT DOCUMENTS 6,228,035 B1 * 5/2001 Packman ........... A61B 5/02233
600/490
10,517,489 B2 12/2019 Narasimhan et al.
(Continued)

OTHER PUBLICATIONS

Chandrasekhar et al., "PPG Sensor Contact Pressure Should Be Taken Into Account for Cuff-Less Blood Pressure Measurement," in IEEE Transactions on Biomedical Engineering, vol. 67, No. 11, pp. 3134-3140, Nov. 2020, doi: 10.1109/TBME.2020.2976989. (Year: 2020).*

(Continued)

*Primary Examiner* — Aurelie H Tu
*Assistant Examiner* — Andrew E Hoffpauir
(74) *Attorney, Agent, or Firm* — F. CHAU & ASSOCIATES, LLC

(57) ABSTRACT

The blood pressure measurement method using a display device includes generating a first pulse wave frequency signal having a magnitude of a pulse wave signal according to a frequency having a fundamental wave component and a harmonics component based on a pressure measurement value and a pulse wave signal, calculating a coefficient of a transfer function based on center frequencies and maximum gains at center frequencies of first harmonics to third harmonics of the first pulse wave frequency signal, generating a second pulse wave frequency signal by blocking noise components of the first harmonics to the third harmonics of the first pulse wave frequency signal based on the transfer function, generating a first pulse wave signal having a magnitude of a pulse wave signal according to a pressure based on the second pulse wave frequency signal, and calculating blood pressure information based on the first pulse wave signal.

16 Claims, 31 Drawing Sheets

(52) U.S. Cl.
CPC ............ *A61B 5/7203* (2013.01); *A61B 5/742*
(2013.01); *A61B 2562/0247* (2013.01)

(58) Field of Classification Search
CPC ............ A61B 5/02438; A61B 5/02444; A61B
5/6897; A61B 5/7203; A61B 5/725; A61B
5/7257; A61B 5/742; A61B 5/7445; A61B
2562/0247
See application file for complete search history.

(56) References Cited

U.S. PATENT DOCUMENTS

| | | | | |
|---|---|---|---|---|
| 10,702,171 | B2 | 7/2020 | Narasimhan et al. | |
| 12,322,205 | B1 * | 6/2025 | Brayman | G06T 7/70 |
| 2003/0009091 | A1 * | 1/2003 | Edgar, Jr. | A61B 5/14551 |
| | | | | 600/323 |
| 2009/0143692 | A1 * | 6/2009 | Brockway | G16H 50/20 |
| | | | | 600/517 |
| 2009/0209868 | A1 * | 8/2009 | Hersh | A61B 5/02225 |
| | | | | 600/485 |
| 2011/0237962 | A1 * | 9/2011 | Hersh | A61B 5/0225 |
| | | | | 600/493 |
| 2014/0278382 | A1 * | 9/2014 | Ricci | H03H 17/0266 |
| | | | | 704/206 |
| 2016/0226505 | A1 * | 8/2016 | Auston | G01R 23/005 |
| 2019/0008399 | A1 * | 1/2019 | Mukkamala | A61B 5/0261 |
| 2019/0021615 | A1 * | 1/2019 | Rundo | A61B 5/725 |
| 2019/0143073 | A1 * | 5/2019 | Grossman | A61B 5/374 |
| | | | | 600/28 |
| 2019/0320986 | A1 * | 10/2019 | Wang | A61B 5/02116 |
| 2021/0121073 | A1 * | 4/2021 | Kuenen | A61B 5/7217 |

OTHER PUBLICATIONS

"Blood pressure measurement by coupling an external pressure and photo-plethysmographic signals," 2020 42nd Annual International Conference of the IEEE Engineering in Medicine & Biology Society (EMBC), Montreal, QC, Canada, 2020, pp. 4996-4999, doi: 10.1109/EMBC44109.2020.9176730. (Year: 2020).*

Wang et al., Estimation of Blood Pressure in the Radial Artery Using Strain-Based Pulse Wave and Photoplethysmography Sensors. Micromachines. 2018; 9(11):556. https://doi.org/10.3390/mi9110556 (Year: 2018).*

Tian J, Xie J, He Z, Ma Q, Wang X (2021), "A device employing a neural network for blood pressure estimation from the oscillatory pressure pulse wave and PPG signal". Sensor Review, vol. 41 No. 1 pp. 74-86, doi: https://doi.org/10.1108/SR-09-2020-0216 (Year: 2021).*

* cited by examiner

FIG. 4
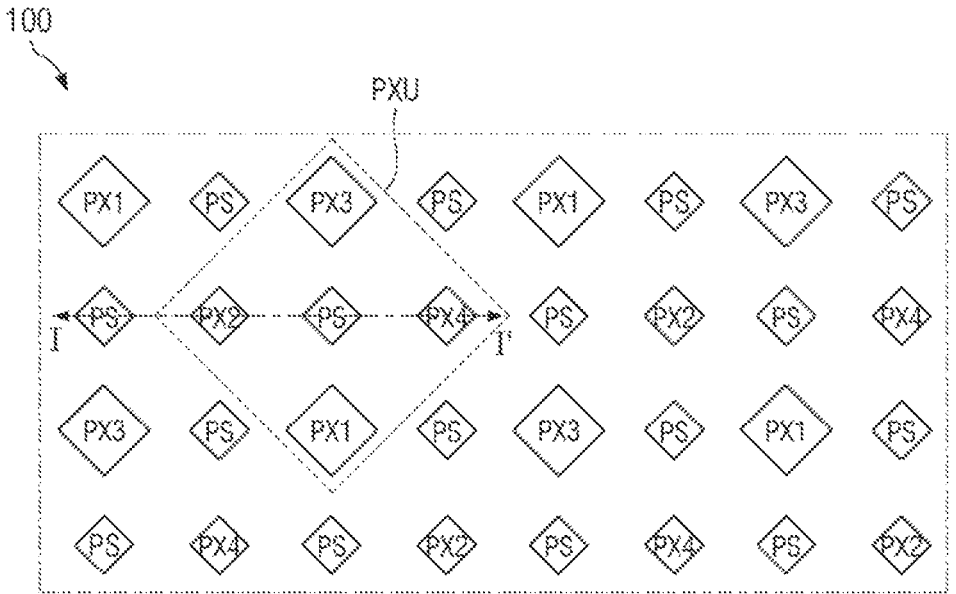
PX: PX1, PX2, PX3, PX4
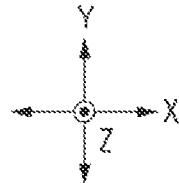

FIG. 7

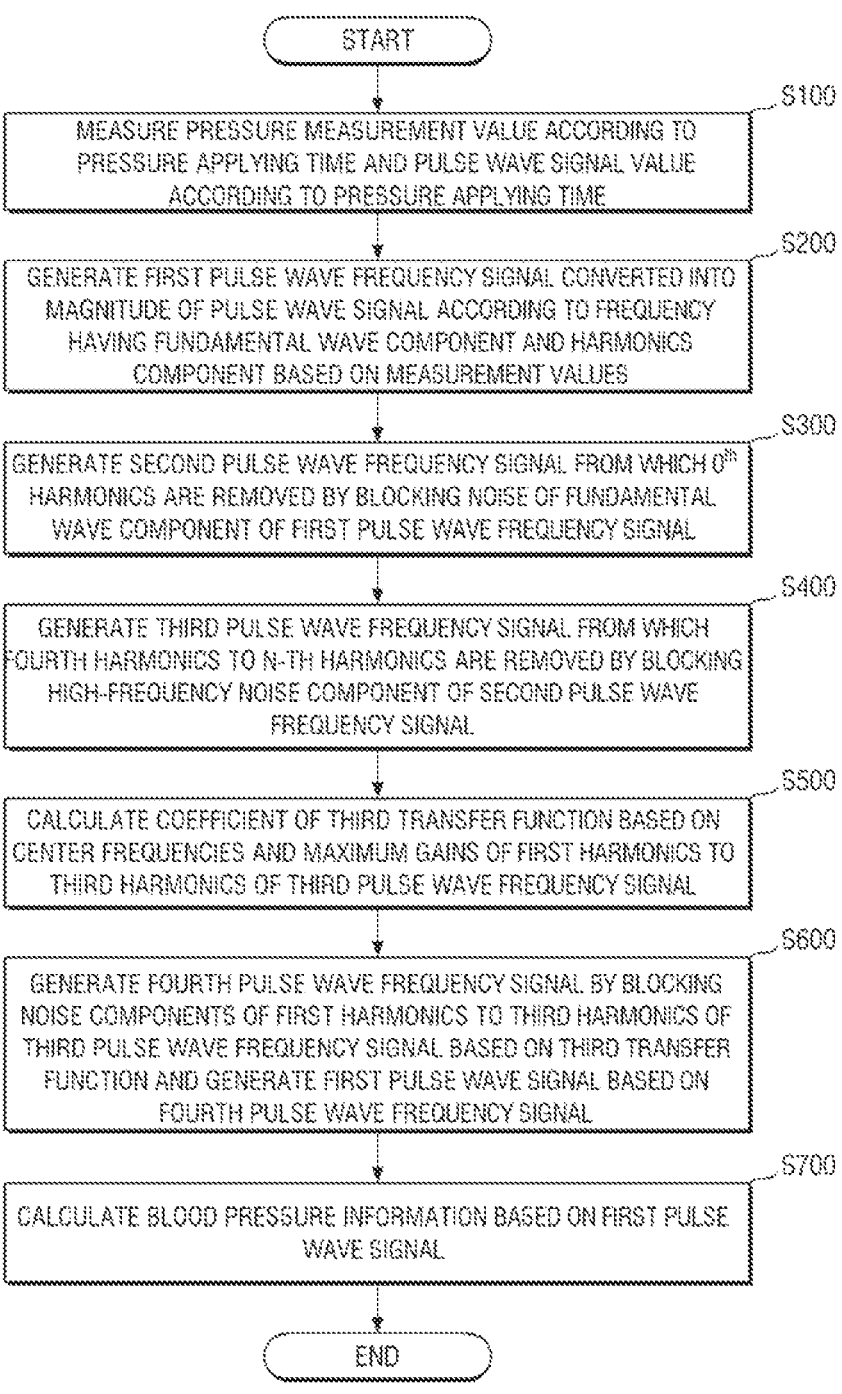

START

MEASURE PRESSURE MEASUREMENT VALUE ACCORDING TO PRESSURE APPLYING TIME AND PULSE WAVE SIGNAL VALUE ACCORDING TO PRESSURE APPLYING TIME — S100

GENERATE FIRST PULSE WAVE FREQUENCY SIGNAL CONVERTED INTO MAGNITUDE OF PULSE WAVE SIGNAL ACCORDING TO FREQUENCY HAVING FUNDAMENTAL WAVE COMPONENT AND HARMONICS COMPONENT BASED ON MEASUREMENT VALUES — S200

GENERATE SECOND PULSE WAVE FREQUENCY SIGNAL FROM WHICH $0^{th}$ HARMONICS ARE REMOVED BY BLOCKING NOISE OF FUNDAMENTAL WAVE COMPONENT OF FIRST PULSE WAVE FREQUENCY SIGNAL — S300

GENERATE THIRD PULSE WAVE FREQUENCY SIGNAL FROM WHICH FOURTH HARMONICS TO N-TH HARMONICS ARE REMOVED BY BLOCKING HIGH-FREQUENCY NOISE COMPONENT OF SECOND PULSE WAVE FREQUENCY SIGNAL — S400

CALCULATE COEFFICIENT OF THIRD TRANSFER FUNCTION BASED ON CENTER FREQUENCIES AND MAXIMUM GAINS OF FIRST HARMONICS TO THIRD HARMONICS OF THIRD PULSE WAVE FREQUENCY SIGNAL — S500

GENERATE FOURTH PULSE WAVE FREQUENCY SIGNAL BY BLOCKING NOISE COMPONENTS OF FIRST HARMONICS TO THIRD HARMONICS OF THIRD PULSE WAVE FREQUENCY SIGNAL BASED ON THIRD TRANSFER FUNCTION AND GENERATE FIRST PULSE WAVE SIGNAL BASED ON FOURTH PULSE WAVE FREQUENCY SIGNAL — S600

CALCULATE BLOOD PRESSURE INFORMATION BASED ON FIRST PULSE WAVE SIGNAL — S700

END

Figure 16:
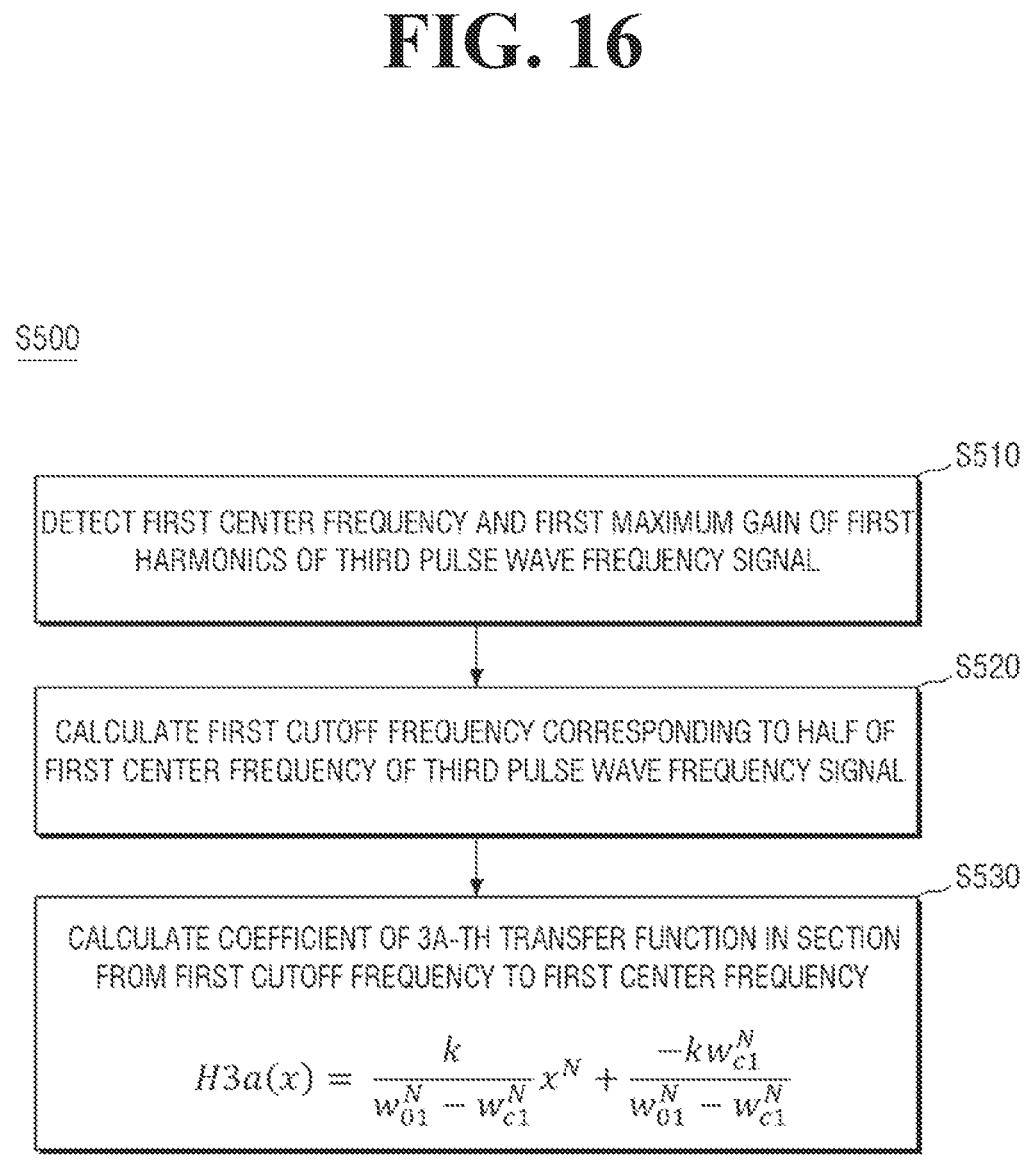

DETECT FIRST CENTER FREQUENCY AND FIRST MAXIMUM GAIN OF FIRST
HARMONICS OF THIRD PULSE WAVE FREQUENCY SIGNAL

S520

CALCULATE FIRST CUTOFF FREQUENCY CORRESPONDING TO HALF OF
FIRST CENTER FREQUENCY OF THIRD PULSE WAVE FREQUENCY SIGNAL

S530

CALCULATE COEFFICIENT OF 3A-TH TRANSFER FUNCTION IN SECTION
FROM FIRST CUTOFF FREQUENCY TO FIRST CENTER FREQUENCY $$H3a(x) = \frac{k}{w_{01}^N - w_{c1}^N} x^N + \frac{-kw_{c1}^N}{w_{01}^N - w_{c1}^N}$$

Figure 18:
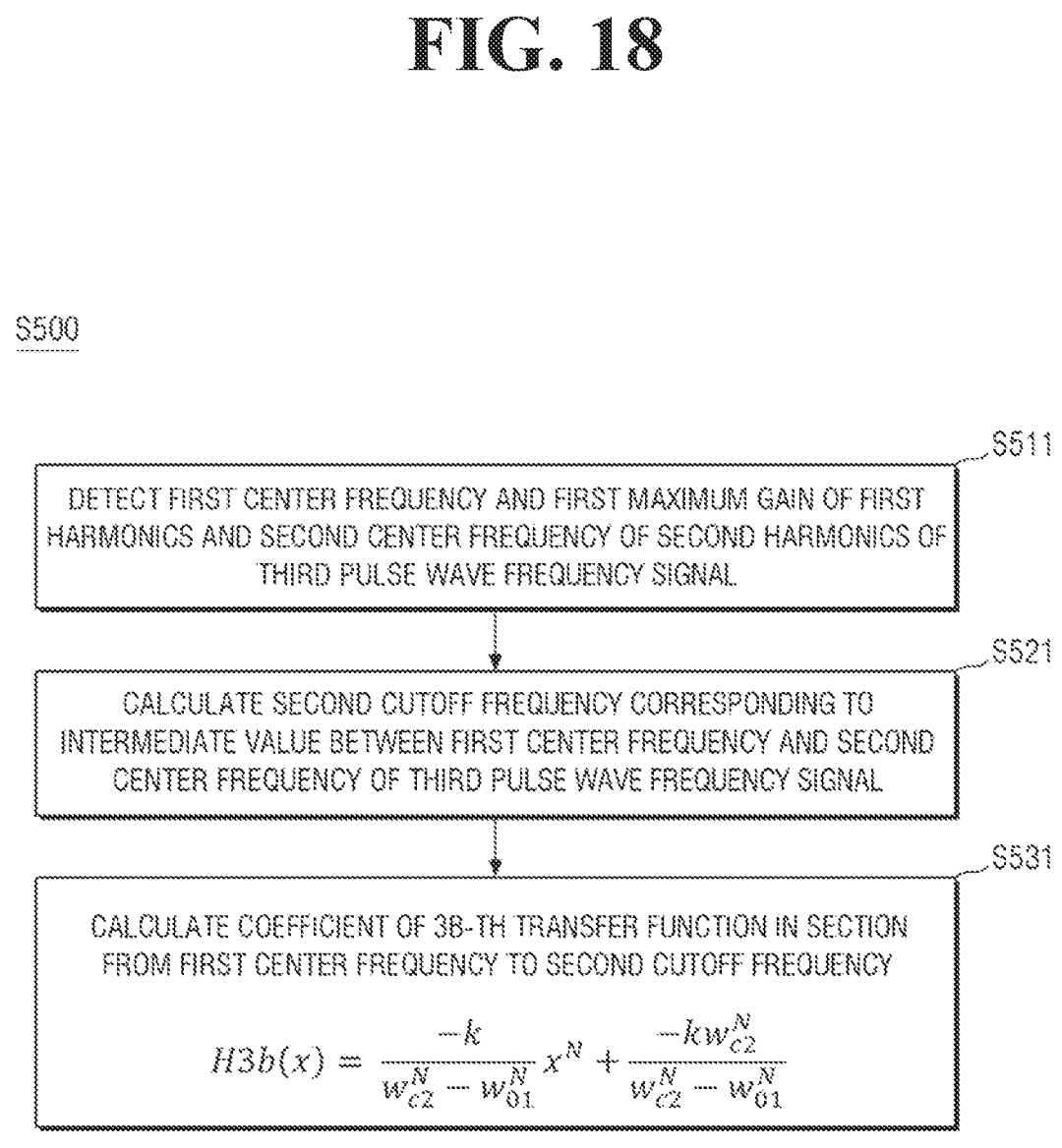

DETECT FIRST CENTER FREQUENCY AND FIRST MAXIMUM GAIN OF FIRST HARMONICS AND SECOND CENTER FREQUENCY OF SECOND HARMONICS OF THIRD PULSE WAVE FREQUENCY SIGNAL

S521

CALCULATE SECOND CUTOFF FREQUENCY CORRESPONDING TO INTERMEDIATE VALUE BETWEEN FIRST CENTER FREQUENCY AND SECOND CENTER FREQUENCY OF THIRD PULSE WAVE FREQUENCY SIGNAL

S531

CALCULATE COEFFICIENT OF 3B-TH TRANSFER FUNCTION IN SECTION FROM FIRST CENTER FREQUENCY TO SECOND CUTOFF FREQUENCY $$H3b(x) = \frac{-k}{w_{c2}^N - w_{01}^N} x^N + \frac{-kw_{c2}^N}{w_{c2}^N - w_{01}^N}$$

Figure 23:
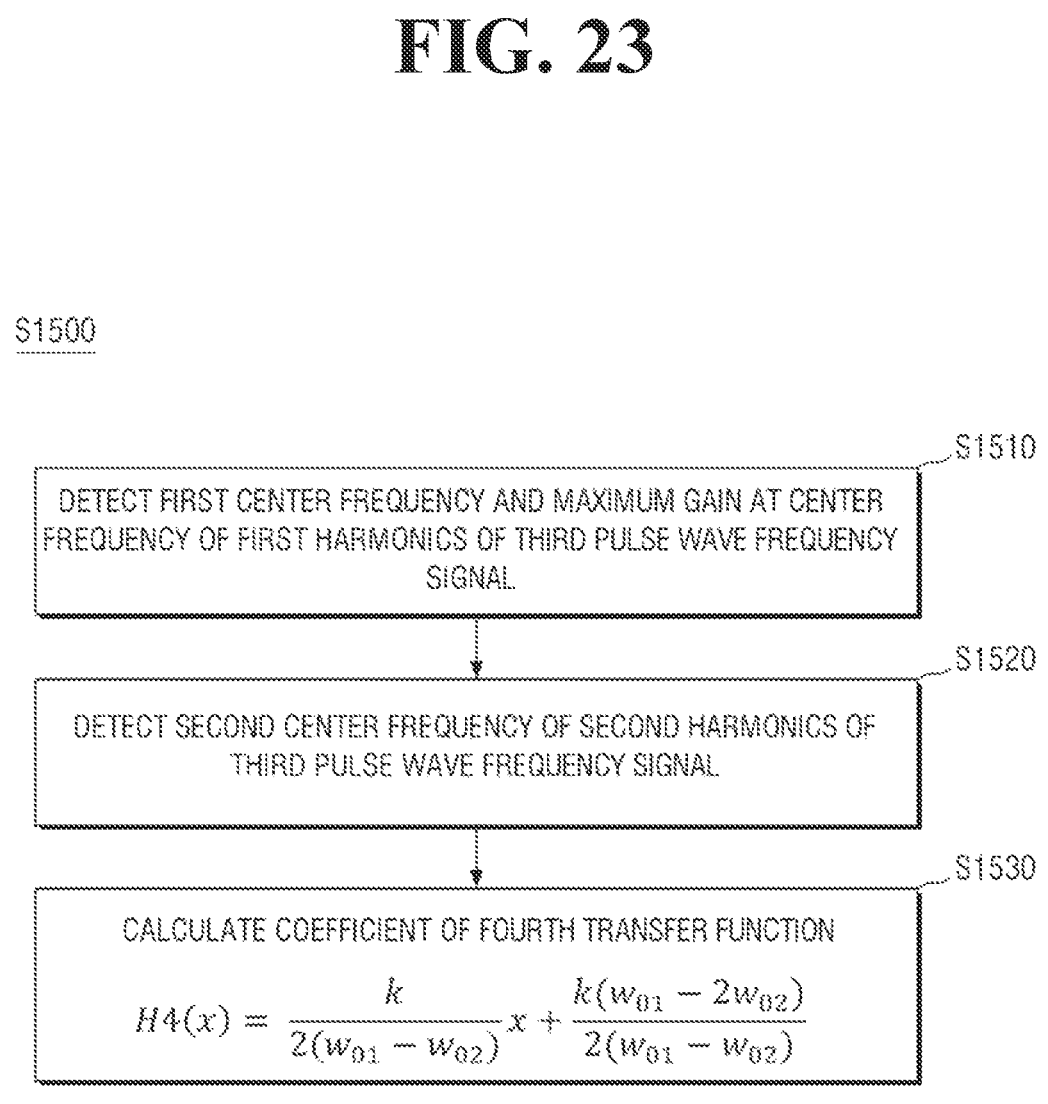

DETECT FIRST CENTER FREQUENCY AND MAXIMUM GAIN AT CENTER FREQUENCY OF FIRST HARMONICS OF THIRD PULSE WAVE FREQUENCY SIGNAL

S1510

DETECT SECOND CENTER FREQUENCY OF SECOND HARMONICS OF THIRD PULSE WAVE FREQUENCY SIGNAL

S1520

CALCULATE COEFFICIENT OF FOURTH TRANSFER FUNCTION $$H4(x) = \frac{k}{2(w_{01} - w_{02})}x + \frac{k(w_{01} - 2w_{02})}{2(w_{01} - w_{02})}$$

S1530

S1500

DETECT SECOND CENTER FREQUENCY AND MAXIMUM GAIN AT CENTER
FREQUENCY OF SECOND HARMONICS OF THIRD PULSE WAVE
FREQUENCY SIGNAL ⟋S1511

DETECT THIRD CENTER FREQUENCY OF THIRD HARMONICS OF THIRD
PULSE WAVE FREQUENCY SIGNAL ⟋S1521

CALCULATE COEFFICIENT OF FIFTH TRANSFER FUNCTION ⟋S1531

$$H5(x) = \frac{k}{2(w_{02} - w_{03})}x + \frac{k(w_{02} - 2w_{03})}{2(w_{02} - w_{03})}$$

DISPLAY DEVICE AND BLOOD PRESSURE MEASUREMENT METHOD USING THE SAME

CROSS-REFERENCE TO RELATED APPLICATION

This application claims priority under 35 U.S.C. § 119 to Korean Patent Application No. 10-2022-0036657 filed on Mar. 24, 2022 in the Korean Intellectual Property Office, the disclosure of which is incorporated by reference herein in its entirety.

TECHNICAL FIELD

The present invention relates to a display device and a blood pressure measurement method using the same.

DISCUSSION OF THE RELATED ART

Display devices are devices that include display screens, and have been used not only in televisions (TVs) and monitors, but also in mobile smartphones and tablet personal computers (PCs). Portable display devices, such as mobile smartphones and tablet PCs, are provided with various functions. Examples of such various functions include a camera function, a fingerprint sensor function, and the like.

In addition, as the healthcare industry has attracted increased attention, methods for more conveniently acquiring biometric information regarding health of a user have been under development. For example, electronic products that can be conveniently carried have been under development to replace a traditional oscillometric pulse measurement device. However, an electronic pulse measurement device may include, for example, an independent light source, a sensor, and a display, and should be separately carried from other devices, which is inconvenient.

SUMMARY

According to an embodiment of the present invention, a blood pressure measurement method using a display device includes: generating a first pulse wave frequency signal having a magnitude of a pulse wave signal according to a frequency having a fundamental wave component and a harmonics component based on a pressure measurement value that is sensed by a pressure sensor and a pulse wave signal that is sensed by a photo-sensor; calculating a coefficient of a transfer function based on center frequencies and maximum gains at center frequencies of first harmonics to third harmonics of the first pulse wave frequency signal; generating a second pulse wave frequency signal by blocking noise components of the first harmonics to the third harmonics of the first pulse wave frequency signal based on the transfer function; generating a first pulse wave signal having a magnitude of a pulse wave signal according to a pressure based on the second pulse wave frequency signal; and calculating blood pressure information based on the first pulse wave signal, wherein the blood pressure information is displayed on a display panel of the display device.

In an embodiment of the present invention, the calculating of the coefficient of the transfer function based on the center frequencies and the maximum gains at the center frequencies of the first harmonics to the third harmonics of the first pulse wave frequency signal includes: detecting a first center frequency and a maximum gain at the first center frequency of the first harmonics of the first pulse wave frequency signal, a second center frequency and a maximum gain at the second center frequency of the second harmonics of the first pulse wave frequency signal, and a third center frequency and a maximum gain at the third center frequency of the third harmonics of the first pulse wave frequency signal; and calculating cutoff frequencies based on the center frequencies.

In an embodiment of the present invention, the calculating of the cutoff frequencies based on the center frequencies includes calculating a first cutoff frequency as corresponding to a half of the first center frequency.

In an embodiment of the present invention, the transfer function includes a first transfer function blocking a noise component of the first harmonics in a section from the first cutoff frequency to the first center frequency, and the first transfer function has a waveform of a convex polynomial function.

In an embodiment of the present invention, the first transfer function is calculated by $$H1(x) = \frac{k}{w_{01}^N - w_{c1}^N} x^N + \frac{-kw_{c1}^N}{w_{01}^N - w_{c1}^N}$$

in which H1(x) is the first transfer function, $w_{o1}$ is the first center frequency, k1 is the maximum gain of the first center frequency, $w_{c1}$ is the first cutoff frequency, and N is a natural number of 2 or more.

In an embodiment of the present invention, the calculating of the cutoff frequencies based on the center frequencies further includes calculating a second cutoff frequency corresponding to an intermediate value between the first center frequency and the second center frequency.

In an embodiment of the present invention, the transfer function includes a second transfer function blocking a noise component of the first harmonics in a section from the first center frequency to the second cutoff frequency, and the second transfer function is calculated by $$H2(x) = \frac{-k}{w_{c2}^N - w_{01}^N} x^N + \frac{-kw_{01}^N}{w_{c2}^N - w_{01}^N}$$

in which H2(x) is the second transfer function, $w_{o1}$ is the first center frequency, k1 is the maximum gain of the first center frequency, $w_{c2}$ is the second cutoff frequency, and N is a natural number of 2 or more.

In an embodiment of the present invention, a maximum gain of the first transfer function is the same as a maximum gain of the second transfer function.

In an embodiment of the present invention, in the calculating of the blood pressure information based on the first pulse wave signal, a peak detection signal is generated using peak values of the first pulse wave signal, a pressure value corresponding to the peak value of the peak detection signal is calculated, and a diastolic blood pressure lower than the pressure value, a systolic blood pressure higher than the pressure value, and a mean blood pressure are calculated according to the pressure value.

In an embodiment of the present invention, a first pressure value and a second pressure value are calculated, wherein the first pressure value is smaller than the pressure value corresponding to about 60% to about 80% of the peak value in the peak detection signal, and the second pressure value is greater than the pressure value, and the first pressure value is calculated as the diastolic blood pressure, and the second pressure value is calculated as the systolic blood pressure.

In an embodiment of the present invention, the blood pressure measurement method further includes generating a second pulse wave frequency signal by blocking noise of the fundamental wave component of the first pulse wave frequency signal.

In an embodiment of the present invention, the fundamental wave component includes a signal having a frequency of 0 hz.

In an embodiment of the present invention, the blood pressure measurement method further includes generating a third pulse wave frequency signal from which fourth harmonics greater than the third harmonics are removed by blocking a high-frequency noise component of the second pulse wave frequency signal.

According to an embodiment of the present invention, a blood pressure measurement method using a display device includes: generating a first pulse wave frequency signal having a magnitude of a pulse wave signal according to a frequency having a fundamental wave component and a harmonics component based on a pressure measurement value that is sensed by a pressure sensor and a pulse wave signal that is sensed by a photo-sensor; calculating a coefficient of a transfer function based on center frequencies and maximum gains at center frequencies of first harmonics to third harmonics of the first pulse wave frequency signal; generating a second pulse wave frequency signal by changing the maximum gains of the first harmonics to the third harmonics of the first pulse wave frequency signal based on the transfer function; generating a second pulse wave signal having a magnitude of a pulse wave signal according to a pressure based on the second pulse wave frequency signal; and calculating blood pressure information based on the second pulse wave signal and displaying the blood pressure information on a display panel of the display device, wherein one cycle of the second pulse wave signal includes a plurality of waveforms having different amplitudes from each other, and a peak value of a first waveform of the plurality of waveforms is greater than a peak value of a second waveform of the plurality of waveforms.

In an embodiment of the present invention, the calculating of the coefficient of the transfer function based on the center frequencies and the maximum gains at the center frequencies of the first harmonics to the third harmonics of the first pulse wave frequency signal includes: calculating a first center frequency and a first maximum gain at the first center frequency of the first harmonics; and calculating a second center frequency of the second harmonics and a third center frequency of the third harmonics.

In an embodiment of the present invention, the transfer function includes a third transfer function in which the peak value of the first waveform is greater than the peak value of the second waveform, and
the third transfer function is calculated by $$H3(x) = \frac{k}{2(w_{01} - w_{02})}x + \frac{k(w_{01} - 2w_{02})}{2(w_{01} - w_{02})}$$

in which $w_{o1}$ is the first center frequency, k is a maximum gain of the first center frequency, and $w_{o2}$ is the second center frequency.

In an embodiment of the present invention, wherein RI=Rp/Sp in which RI is a reflected pulse wave ratio, Sp is a pulse wave contraction value, Rp is a reflected pulse wave value, wherein the pulse wave contraction value is the peak value of the first waveform of the plurality of waveforms, and the reflected pulse wave value is the peak value of the second waveform of the plurality of waveforms.

In an embodiment of the present invention, the reflected pulse wave ratio includes a first period in which the reflected pulse wave ratio fluctuates within a first range, a second period in which the reflected pulse wave ratio fluctuates within a second range, and a third period in which the reflected pulse wave ratio fluctuates within a third range, and wherein a width of the first range and a width of the third range are smaller than a width of the second range.

In an embodiment of the present invention, the reflected pulse wave ratio is analyzed to detect a start point in time of the second period, wherein a third pressure value corresponding to the second pulse wave signal at the start point in time of the second period is calculated and set as a diastolic blood pressure, and wherein a fourth pressure value corresponding to the second pulse wave signal at a start point in time of the third period after the second period is calculated and set as a systolic blood pressure.

According to an embodiment of the present invention, a display device includes: a display panel including pixels displaying an image; a pressure sensor disposed on the display panel and sensing a pressure applied from outside of the display device; a photo-sensor disposed on the display panel and sensing light; and a main processor receiving a pressure measurement value that is sensed by the pressure sensor and a pulse wave signal that is sensed by the photo-sensor, wherein the main processor generates a first pulse wave frequency signal having a fundamental wave component and a harmonics component according to the pressure measurement value and the pulse wave signal, generates a second pulse wave frequency signal by blocking noise of the harmonics component of the first pulse wave frequency signal, generates a first pulse wave signal based on the second pulse wave frequency signal, and calculates blood pressure information based on the first pulse wave signal, and wherein each of the first pulse wave frequency signal and the second pulse wave frequency signal is a magnitude of the pulse wave signal according to a frequency, and the first pulse wave signal is a magnitude of the pulse wave signal according to the pressure measurement value.

BRIEF DESCRIPTION OF THE DRAWINGS

The above and other features of the present invention will become more apparent by describing in detail embodiments thereof with reference to the attached drawings, in which:

FIG. 4 is a plan layout view of pixels and photo-sensors of a display cell according to an embodiment of the present invention;

FIG. 7 is a flowchart illustrating a blood pressure measurement method using the display device according to an embodiment of the present invention;

FIG. 16 is a flowchart illustrating a method of calculating a coefficient of a 3*a*-th transfer function according to an embodiment of the present invention;

FIG. 18 is a flowchart illustrating a method of calculating a coefficient of a 3*b*-th transfer function according to an embodiment of the present invention;

FIG. 23 is a flowchart illustrating a method of calculating a coefficient of a fourth transfer function according to an embodiment of the present invention.

DETAILED DESCRIPTION OF THE EMBODIMENTS

The present invention will now be described more fully hereinafter with reference to the accompanying drawings, in which preferred embodiments of the invention are shown. This invention may, however, be embodied in different forms and should not be construed as being limited to the embodiments set forth herein.

It will also be understood that when a layer is referred to as being "on" another layer or substrate, it can be directly on the other layer or substrate, or intervening layers may also be present. The same reference numbers may indicate the same components throughout the specification, and thus, repetitive descriptions may be omitted.

It will be understood that, although the terms "first," "second," etc. may be used herein to describe various elements, these elements should not be limited by these terms. These terms are only used to distinguish one element from another element. For instance, a first element discussed below could be termed a second element without departing from the spirit and scope of the present invention. Similarly, the second element could also be termed the first element.

Hereinafter, embodiments of the present invention will be described with reference to the accompanying drawings.

Figure 1:
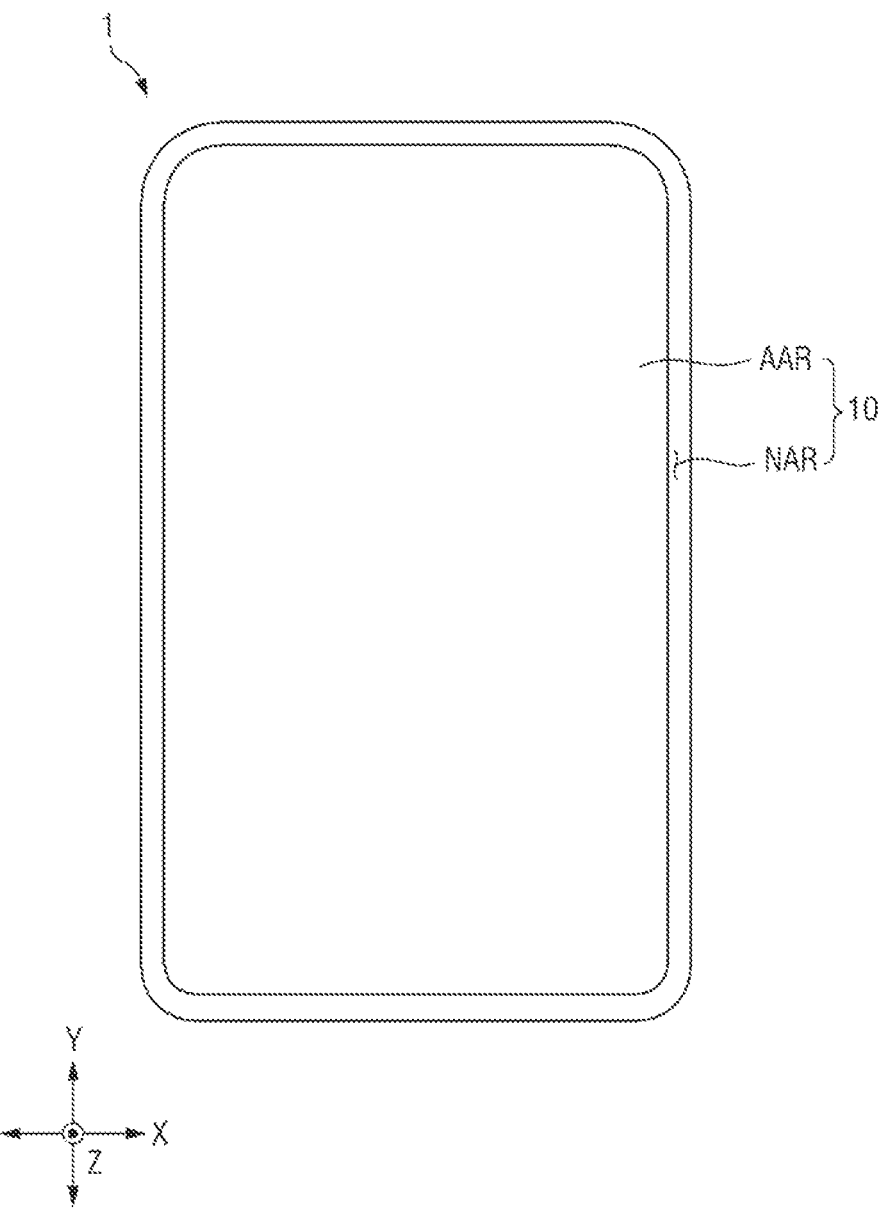
FIG. 1 is a plan view of a display device according to an embodiment of the present invention.
Figure 2:
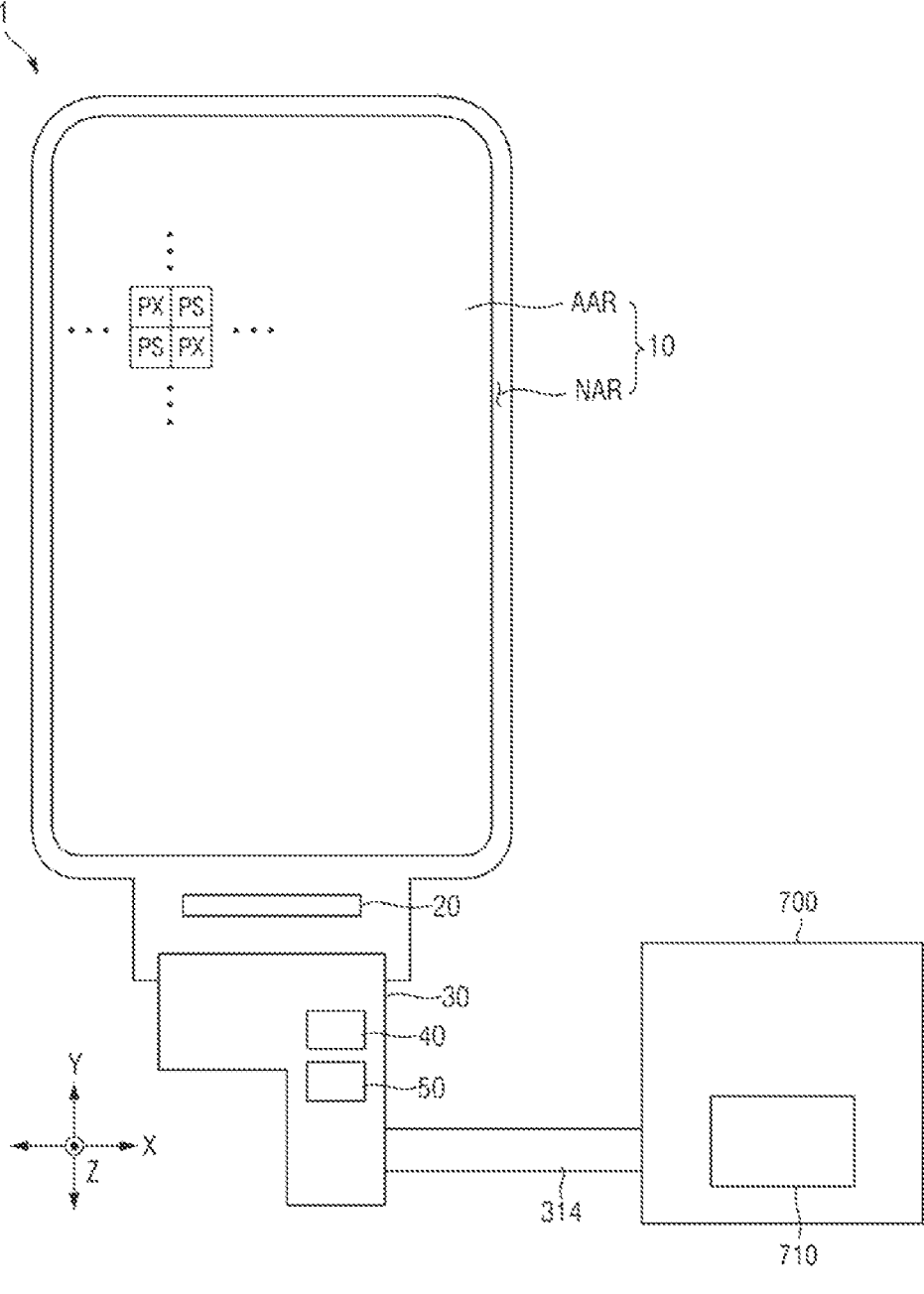
FIG. 2 is a plan view of the display device according to an embodiment of the present invention.

FIG. 1 is a plan view of a display device according to an embodiment of the present invention. FIG. 2 is a plan view of the display device according to an embodiment of the present invention.

Referring to FIGS. 1 and 2, a display device 1 may include various electronic devices providing a display screen. Examples of the display device 1 may include, but are limited to, mobile phones, smartphones, tablet personal computers (PCs), mobile communication terminals, electronic notebooks, electronic books, personal digital assistants (PDAs), portable multimedia players (PMPs), navigation devices, ultra mobile PCs (UMPCs), televisions, game machines, wrist watch-type electronic devices, head-mounted displays, monitors of personal computers, laptop computers, vehicle instrument boards, digital cameras, camcorders, external billboards, electric signs, various medical devices, various inspection devices, various home appliances including display areas, such as refrigerators and washing machines, Internet of Things (IoT) devices, or the like. Representative examples of a display device 1 to be described later may include, but are not limited to, smartphones, tablet PCs, laptop computers, or the like.

The display device 1 may include a display panel 10, a display driver 20, a circuit board 30, a pulse wave sensing circuit 50, a pressure sensing circuit 40, a main circuit board 700, and a main processor 710.

The display panel 10 may include an active area AAR and a non-active area NAR The active area AAR includes a display area in which a screen that provides an image is formed. For example, the active area AAR may completely overlap the display area. A plurality of pixels PX displaying an image may be disposed in the display area. Each pixel PX may include a light emitting unit emitting light.

The active area AAR further includes a light sensing area. The light sensing area is an area responding to light, and is an area configured to sense an amount, a wavelength, intensity, or the like, of incident light. The light sensing area may overlap the display area. In an embodiment of the present invention, the light sensing area may completely overlap the active area AAR in plan view. In this case, the area of the light sensing area and the area of the display area may be the same size as each other. In an embodiment of the present invention, the light sensing area may be disposed in only a portion of the active area AAR. For example, the light sensing area may be disposed in only a limited area for fingerprint recognition. In this case, the light sensing area may overlap a portion of the display area, but might not overlap another portion of the display area.

A plurality of photo-sensors PS responding to light may be disposed in the light sensing area.

The non-active area NAR may be disposed around the active area AAR. The display driver 20 may be disposed in the non-active area NAR. The display driver 20 may drive the plurality of pixels PX and/or the plurality of photo-sensors PS. The display driver 20 may output signals and voltages for driving the display panel 10. The display driver 20 may be formed as an integrated circuit (IC) and be mounted on the display panel 10. Signal lines for transferring signals between the display driver 20 and the active area AAR may be disposed in the non-active area NAR. As another example, the display driver 20 may be mounted on the circuit board 30.

The circuit board 30 may be attached to one end of the display panel 10 using an anisotropic conductive film (ACF). Lead lines of the circuit board 30 may be electrically connected to pad parts of the display panel 10. The circuit board 30 may be a flexible printed circuit board or a flexible film such as a chip on film.

The pulse wave sensing circuit 50 may be disposed on the circuit board 30. For example, the pulse wave sensing circuit 50 may be formed as an integrated circuit and be attached to an upper surface of the circuit board 30. The pulse wave sensing circuit 50 may be connected to a display layer of the display panel 10. The pulse wave sensing circuit 50 may sense a photocurrent generated by photons of light incident on the plurality of photo-sensors PS of the display panel 10. The pulse wave sensing circuit 50 may recognize a pulse wave of a user based on the photocurrent.

The pressure sensing circuit 40 may be disposed on the circuit board 30. For example, the pressure sensing circuit 40 may be formed as an integrated circuit and be attached to the upper surface of the circuit board 30. The pressure sensing circuit 40 may be connected to the display layer of the display panel 10. The pressure sensing circuit 40 may sense electrical signals by pressures applied to a plurality of pressure sensors of the display panel 10. The pressure sensing circuit 40 may generate pressure data according to a change in the electrical signal sensed by the pressure sensor, and transmit the pressure data to the main processor 710.

The main circuit board 700 may be a printed circuit board or a flexible printed circuit board.

The main circuit board 700 may include the main processor 710.

The main processor 710 may control all functions of the display device 1. For example, the main processor 710 may output digital video data to the display driver 20 through the circuit board 30 so that the display panel 10 displays an image. In addition, the main processor 710 may receive touch data from a touch driving circuit, determine touch coordinates of a touch input of the user, and then execute an application indicated by an icon displayed on the touch coordinates of the user.

The main processor 710 may calculate a pulse wave signal PPG reflecting a blood change depending on a heartbeat detected according to an optical signal input from the pulse wave sensing circuit 50. In addition, the main processor 710 may calculate a touch pressure of the user according to the electrical signal input from the pressure sensing circuit 40. In addition, the main processor 710 may calculate a blood pressure of the user based on the pulse wave signal PPG and a pressure signal. In this case, the main processor 710 may calculate the blood pressure by blocking noise components generated for each user by a filter unit 800. A description thereof will be provided later.

The main processor 710 may be an application processor formed of an integrated circuit, a central processing unit, or a system chip.

In addition, a mobile communication module capable of transmitting and receiving wireless signals to and from at least one of a base station, an external terminal, and a server over a mobile communication network may be mounted on the main circuit board 700. The wireless signal may include various types of data according to transmission/reception of a voice signal, a video call signal, or a text/multimedia message.

Figure 3:
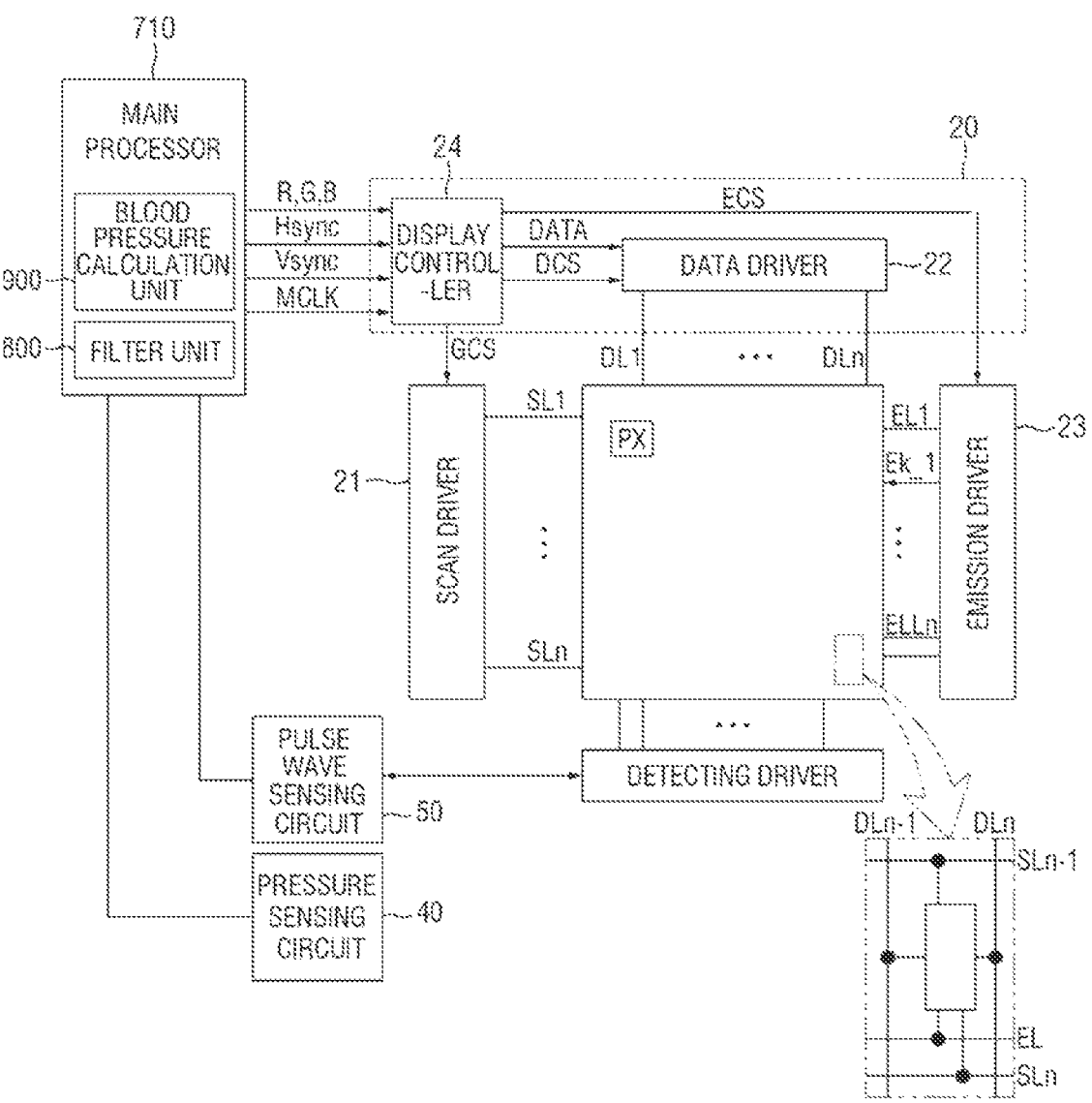
FIG. 3 is a block diagram illustrating the display device according to an embodiment of the present invention.

FIG. 3 is a block diagram illustrating the display device according to an embodiment of the present invention.

Referring to FIG. 3, the display device 1 includes the display panel 10 including the plurality of pixels PX, the display driver 20, a scan driver 21, an emission driver 23, the pulse wave sensing circuit 50, the pressure sensing circuit 40, and the main processor 710.

The main processor 710 includes a filter unit 800 and a blood pressure calculation unit (e.g., circuit) 900.

The filter unit (e.g., circuit) 800 may receive the optical signal from the pulse wave sensing circuit 50. In addition, the filter unit 800 may receive the electrical signal (e.g., a pressure sensing signal) from the pressure sensing circuit 40. The filter unit 800 may generate a pulse wave frequency signal in which noise components for each user are blocked based on the received signals. The filter unit 800 may calculate the pulse wave signal PPG reflecting the blood change depending on the heartbeat of the user determined according to the pulse wave frequency signal. The filter unit 800 may output the pulse wave signal PPG to the blood pressure calculation unit 900. A detailed description of the filter unit 800 will be provided later with reference to FIG. 6.

The blood pressure calculation unit 900 may receive the pulse wave signal PPG from the filter unit 800. The blood pressure calculation unit 900 may calculate a blood pressure of the user based on the pulse wave signal PPG.

The main processor 710 drives and controls the pulse wave sensing circuit 50, the pressure sensing circuit 40, and a display controller 24. The main processor 710 may output image information to the display controller 24. For example, the main processor 710 may output image information including the calculated pulse wave signal PPG, a blood pressure measurement value, and blood pressure information to the display controller 24.

The display controller 24 receives the image signal supplied from the main processor 710. In addition, the display controller 24 may generate a scan control signal GCS for controlling an operation timing of the scan driver 21, an emission control signal ECS for controlling an operation timing of the emission driver 23, and a data control signal DCS for controlling an operation timing of a data driver 22. The display controller 24 may output image data DATA and the data control signal DCS to the data driver 22. The display controller 24 may output the scan control signal GCS to the scan driver 21 and output the emission control signal ECS to the emission driver 23.

The display controller 24 may be electrically connected to the display panel 10 and/or the main processor 710 through lines or may be connected to the display panel 10 and/or the main processor 710 through a communication network. In an embodiment of the present invention, at least a portion of the display controller 24 may be directly attached to the display panel 10 in the form of a driving chip.

The data driver 22 may receive the image data DATA and the data control signal DCS from the display controller 24. The data driver 22 may convert the image data DATA into analog data voltages according to the data control signal DCS. The data driver 22 may output the converted analog data voltages to data lines DL in synchronization with scan signals provided to the scan lines SL.

The scan driver 21 may generate scan signals according to the scan control signal SCS, respectively, and sequentially output the scan signals to scan lines SL1 to SLn.

The display device 1 may further include a driving voltage, a common voltage and a source voltage line. The source voltage line may include a driving voltage line and a common voltage line. For example, the driving voltage may be a high potential voltage for driving light emitting elements and photoelectric conversion elements, and the common voltage may be a low potential voltage for driving the light emitting elements and the photoelectric conversion elements. For example, the driving voltage may have a higher potential than the common voltage.

A display control signal may include the scan control signal SCS, the data control signal DCS, and the emission control signal ECS. The display control signal may be output from the scan driver 21 and the data driver 22.

The emission driver 23 may generate emission signals Ek_1 according to the emission control signal ECS, and sequentially output the emission signals Ek_1 to emission lines ELL. In addition, it has been illustrated that the emission driver 23 exists separately from the scan driver 21, but the present invention is not limited thereto, and the emission driver 23 may be included in the scan driver 21.

The data driver 22 and the display controller 24 may be included in the display driver 20 that controls an operation of the display panel 10. The data driver 22 and the display controller 24 may be formed as integrated circuits (ICs) and be mounted on the display driver 20.

Each of the plurality of pixels PX may be connected to at least one of the scan lines SL1 to SLn, any one of the data lines DL, and at least one of the emission lines ELL.

Each of the plurality of photo-sensors PS may be connected to any one of the scan lines SL1 to SLn and any one of lead-out lines ROL.

A plurality of scan lines SL1 to SLn may connect the scan driver 21 to the plurality of pixels PX and the plurality of photo-sensors PS, respectively. The plurality of scan lines SL1 to SLn may provide the scan signals output from the scan driver 21 to the plurality of pixels PX, respectively.

A plurality of data lines DL may connect the data driver 22 to the plurality of pixels PX, respectively. The plurality of data lines DL may provide the image data DATA output from the data driver 22 to the plurality of pixels PX, respectively.

A plurality of emission lines ELL may connect the emission driver 23 to the plurality of pixels PX, respectively. The plurality of emission lines ELL may provide the emission control signals ECS output from the emission driver 23 to the plurality of pixels PX, respectively.

FIG. 4 is a plan layout view of pixels and photo-sensors of a display cell according to an embodiment of the present invention.

Referring to FIG. 4, a plurality of pixels PX and a plurality of photo-sensors PS may be repeatedly disposed in a display cell 100.

The plurality of pixels PX: PX1, PX2, PX3, and PX4 may include first pixels PX1, second pixels PX2, third pixels PX3, and fourth pixels PX4. For example, the first pixel PX1 may emit light of a red wavelength, the second pixel PX2 and the fourth pixel PX4 may emit light of a green wavelength, and the third pixel PX3 may emit light of a blue wavelength. The plurality of pixels PX may include a plurality of emission areas emitting light, respectively. The plurality of photo-sensors PS may include a plurality of light sensing areas sensing light incident thereon.

The first pixels PX1, the second pixels PX2, the third pixels PX3, and the fourth pixels PX4 and the plurality of photo-sensors PS may be alternately arranged in a first direction X and a second direction Y. For example, the photo-sensor PS may be positioned between the first pixel PX1 and the third pixel PX3, and may be positioned between the second pixel PX2 and the fourth pixel PX4. In an embodiment of the present invention, the first pixels PX1 and the third pixels PX3 may be alternately arranged while forming a first row along the first direction X, and the second pixels PX2 and the fourth pixels PX4 may be alternately arranged along the first direction X in a second row adjacent to the first row. Pixels PX belonging to the first row may be disposed to be misaligned with pixels PX belonging to the second row in the first direction X. Arrangements of the first row and the second row may be repeated up to an n-th row.

The photo-sensors PS may be disposed to be spaced apart from each other between the first pixels PX1 and the third pixels PX3 forming the first row. The first pixels PX1, the photo-sensors PS, and the third pixels PX3 may be alternately arranged along the first direction X. The photo-sensors PS may be disposed to be spaced apart from each other between the second pixels PX2 and the fourth pixels PX4 forming the second row. The second pixels PX2, the photo-sensors PS, and the fourth pixels PX4 may be alternately arranged along the first direction X. The number of photo-sensors PS in the first row may be the same as the number of photo-sensors PS in the second row. Arrangements of the first row and the second row may be repeated up to an n-th row.

As another example, the photo-sensors PS may be disposed between the second pixels PX2 and the fourth pixels PX4 forming the second row, and might not be disposed between the first pixels PX1 and the third pixels PX3 forming the first row. That is, the photo-sensors PS might not be disposed in the first row.

Sizes of emission areas of the respective pixels PX may be different from each other. Sizes of emission areas of the second pixel PX2 and the fourth pixel PX4 may be smaller than each of emission areas of the first pixel PX1 and the third pixel PX3. It has been illustrated that the respective pixels PX have, for example, a rhombic shape, but the present invention is not limited thereto, and the respective pixels PX have may have a rectangular shape, an octagonal shape, a circular shape, or other polygonal shapes.

One pixel unit PXU may include one first pixel PX1, one second pixel PX2, one third pixel PX3, and one fourth pixel PX4. The pixel unit PXU refers to a group of color pixels capable of expressing a gradation.

Figure 5:
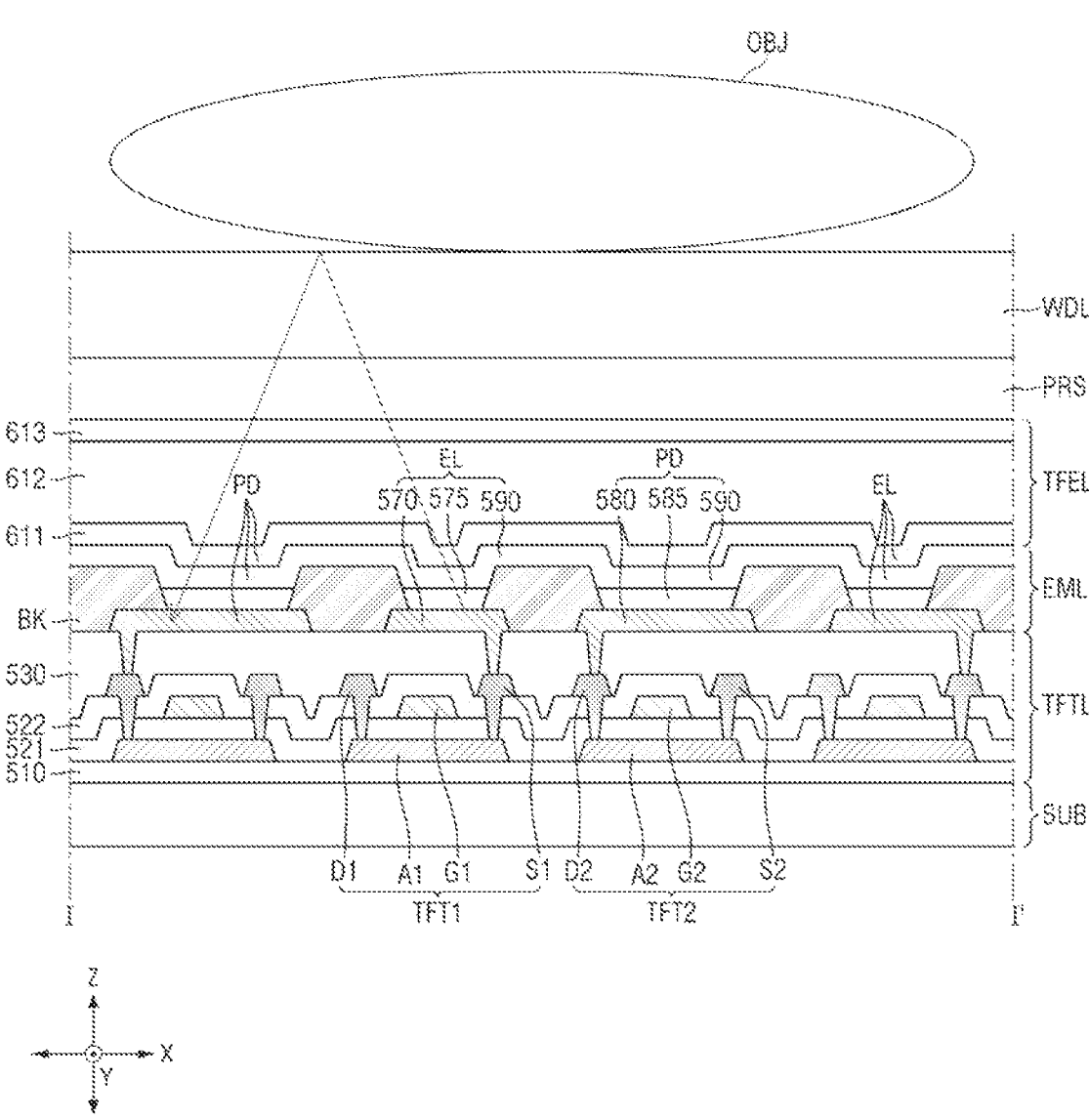
FIG. 5 is a cross-sectional view taken along line I-I' of FIG. 4.

FIG. 5 is a cross-sectional view taken along line I-I' of FIG. 4.

Referring to FIG. 5, a buffer layer 510 is disposed on a substrate SUB. The buffer layer 510 may include, for example, silicon nitride, silicon oxide, silicon oxynitride, or the like.

A first thin film transistor TFT1 and a second thin film transistor TFT2 may be disposed on the buffer layer 510.

A plurality of thin film transistors TFT1 and TFT2 may include, respectively, semiconductor layers A1 and A2, a gate insulating layer 521, gate electrodes G1 and G2, an interlayer insulating film 522, source electrodes S1 and S2, drain electrodes D1 and D2. The gate insulating layer 52 may be disposed on at least portions of the semiconductor layers A1 and A2. The gate electrodes G1 and G2 may be disposed on the gate insulating layer 521. The interlayer insulating film 522 may cover each of the semiconductor layers A1 and A2 and each of the gate electrodes G1 and G2, and the source electrodes S1 and S2 and drain electrodes D1 and D2 may be disposed on the interlayer insulating film 522.

The semiconductor layers A1 and A2 may form channels of the first thin film transistor TFT1 and the second thin film transistor TFT2, respectively. The semiconductor layers A1 and A2 may include polycrystalline silicon. In an embodiment of the present invention, the semiconductor layers A1 and A2 may include single crystal silicon, low-temperature polycrystalline silicon, amorphous silicon, or an oxide semiconductor. The oxide semiconductor may include, for example, a binary compound $(AB_x)$, a ternary compound $(AB_xC_y)$, or a quaternary compound $(AB_xC_yD_z)$ including indium, zinc, gallium, tin, titanium, aluminum, hafnium (Hf), zirconium (Zr), magnesium (Mg), and the like. The semiconductor layers A1 and A2 may include channel regions and source regions and drain regions doped with impurities, respectively.

The gate insulating layer 521 is disposed on the semiconductor layers A1 and A2. The gate insulating layer 521 electrically insulates a first gate electrode G1 and a first semiconductor layer A1 from each other, and electrically insulates a second gate electrode G2 and a second semiconductor layer A2 from each other. The gate insulating layer 521 may be made of an insulating material, for example, silicon oxide $(SiO_x)$, silicon nitride $(SiN_x)$, or metal oxide.

The first gate electrode G1 of the first thin film transistor TFT1 and the second gate electrode G2 of the second thin film transistor TFT2 are disposed on the gate insulating layer 521. The gate electrodes G1 and G2 may be formed above the channel regions of the semiconductor layers A1 and A2, that is, on positions of the gate insulating layer 521 overlapping the channel regions, respectively. For example, the gate electrodes G1 and G2 may respectively overlap the channel regions of the semiconductor layers A1 and A2.

The interlayer insulating film 522 may be disposed on the gate electrodes G1 and G2. The interlayer insulating film 522 may include an inorganic insulating material such as silicon oxide $(SiO_x)$, silicon nitride $(SiN_x)$, silicon oxynitride, hafnium oxide, or aluminum oxide. In addition, the interlayer insulating film 522 may include a plurality of insulating films, and may further include a conductive layer disposed between the insulating films and may form a second electrode to form a capacitor.

The source electrodes S1 and S2 and the drain electrodes D1 and D2 are disposed on the interlayer insulating film 522. A first source electrode S1 of the first thin film transistor TFT1 may be electrically connected to the drain region of the first semiconductor layer A1 through a contact hole penetrating through the interlayer insulating film 522 and the gate insulating layer 521. A second source electrode S2 of the second thin film transistor TFT2 may be electrically connected to the drain region of the second semiconductor layer A2 through a contact hole penetrating through the interlayer insulating film 522 and the gate insulating layer 521. Each of the source electrodes S1 and S2 and the drain electrodes D1 and D2 may include, for example, at least one of aluminum (Al), molybdenum (Mo), platinum (Pt), palladium (Pd), silver (Ag), magnesium (Mg), gold (Au), nickel (Ni), neodymium (Nd), iridium (Ir), chromium (Cr), calcium (Ca), titanium (Ti), tantalum (Ta), tungsten (W), and/or copper (Cu).

A planarization layer 530 may be formed on the interlayer insulating film 522 to cover each of the source electrodes S1 and S2 and the drain electrodes D1 and D2. The planarization layer 530 may be made of an organic insulating material or the like. The planarization layer 530 may have a flat surface and include contact holes exposing any one of the source electrodes S1 and S2 and any one of the drain electrodes D1 and D2.

A light emitting element layer EML may be disposed on the planarization layer 530. The light emitting element layer EML may include light emitting elements EL, photoelectric conversion elements PD, and a bank layer BK. The light emitting element EL may include a pixel electrode 570, an emission layer 575, and a common electrode 590, and the photoelectric conversion element PD may include a first electrode 580, a photoelectric conversion layer 585, and a common electrode 590.

The pixel electrode 570 of the light emitting element EL may be disposed on the planarization layer 530. The pixel electrode 570 may be provided for each pixel PX. The pixel electrode 570 may be connected to the first source electrode S1 or the first drain electrode D1 of the first thin film transistor TFT1 through a contact hole penetrating through the planarization layer 530.

The pixel electrode 570 of the light emitting element EL may have a single-layer structure of, for example, molybdenum (Mo), titanium (Ti), copper (Cu), or aluminum (Al) or have a stacked film structure, for example, a multilayer structure of ITO/Mg, ITO/MgF, ITO/Ag, or ITO/Ag/ITO including indium-tin-oxide (ITO), indium-zinc-oxide (IZO), zinc oxide (ZnO), or indium oxide $(In_2O_3)$, and silver (Ag), magnesium (Mg), aluminum (Al), platinum (Pt), lead (Pb), gold (Au), and/or nickel (Ni), but the present invention is not limited thereto.

The first electrode 580 of the photoelectric conversion element PD may be disposed on the planarization layer 530. The first electrode 580 may be provided for each photosensor PS. The first electrode 580 may be connected to the second source electrode S2 or the second drain electrode D2 of the second thin film transistor TFT2 through a contact hole penetrating through the planarization layer 530.

The first electrode 580 of the photoelectric conversion element PD may have a single-layer structure of, for example, molybdenum (Mo), titanium (Ti), copper (Cu), or aluminum (Al) or have a multilayer structure of, for example, ITO/Mg, ITO/MgF, ITO/Ag, or ITO/Ag/ITO, but the present invention is not limited thereto.

The bank layer BK may be disposed on the pixel electrode 570 and the first electrode 580. The bank layer BK may include openings formed in areas overlapping the pixel electrodes 570 and exposing at least a portion of the pixel electrodes 570. Areas in which the exposed portions of the pixel electrodes 570 and the emission layers 575 overlap each other may be defined as emission areas emitting different light according to the respective pixels PX: PX1, PX2, PX3, and PX4.

In addition, the bank layer BK may include openings formed in areas overlapping the first electrodes 580 and exposing the first electrodes 580. The openings exposing the first electrodes 580 may provide spaces in which the photoelectric conversion layers 585 of the respective photosensors PS are formed, and areas in which the exposed first electrodes 580 and the photoelectric conversion layers 585 overlap each other may be defined as light sensing parts RA.

The bank layer BK may include an organic insulating material such as a polyacrylates resin, an epoxy resin, a phenolic resin, a polyamides resin, a polyimides resin, an unsaturated polyesters resin, a polyphenyleneethers resin, a polyphenylenesulfides resin, or benzocyclobutene (BCB). As another example, the bank layer BK may also include an inorganic material such as silicon nitride.

The emission layers 575 may be disposed on the pixel electrodes 570 of the light emitting elements EL exposed by the openings of the bank layer BK. The emission layer 575 may include a high molecular material or a low molecular material, and may emit red, green, or blue light for each pixel PX. The light emitted from the emission layer 575 may contribute to displaying an image or function as a light source for light incident on the photo-sensor PS. For example, light sources of a green wavelength emitted from the emission areas of the second pixel PX2 and the fourth pixel PX4 may function as light sources of light incident on the light sensing areas of the photo-sensors PS.

When the emission layer 575 is formed of an organic material, a hole injecting layer (HIL) and a hole transporting layer (HTL) may be disposed at a lower portion of each emission layer 575, and an electron injecting layer (EIL) and an electron transporting layer (ETL) may be stacked at an upper portion of each emission layer 575. Each of these layers may be a single layer or a multiple layer made of an organic material.

The photoelectric conversion layers 585 may be disposed on the portions of the first electrodes 580 of the photoelectric conversion elements PD exposed by the openings of the bank layer BK. Areas in which the exposed portions of the first electrodes 580 and the photoelectric conversion layers 585 overlap each other may be defined as light sensing areas of the respective photo-sensors PS. The photoelectric conversion layer 585 may generate photocharges in proportion to incident light. The incident light may be light emitted from the emission layer 575 and then reflected to enter the photoelectric conversion layer 585 or may be light provided from the outside regardless of the emission layer 575. Charges generated and accumulated in the photoelectric conversion layer 585 may be converted into electrical signals for sensing.

The photoelectric conversion layer 585 may include an electron donating material and an electron accepting material. The electron donating material may generate donor ions in response to light, and the electron accepting material may generate acceptor ions in response to light. When the photoelectric conversion layer 585 is formed of an organic material, the electron donating material may include a compound such as subphthalocyanine (SubPc) or dibutylphosphate (DBP), but the present invention is not limited thereto. The electron accepting material may include a compound such as fullerene, a fullerene derivative, or perylene diimide, but is not limited thereto.

In addition, when the photoelectric conversion layer 585 is formed of an inorganic material, the photoelectric conversion element PD may be a pn-type or pin-type phototransistor. For example, the photoelectric conversion layer 585 may have a structure in which an N-type semiconductor layer, an I-type semiconductor layer, and a P-type semiconductor layer are sequentially stacked on each other.

When the photoelectric conversion layer 585 is formed of the organic material, a hole injecting layer (HIL) and a hole transporting layer (HTL) may be disposed at a lower portion of each photoelectric conversion layer 585, and an electron injecting layer (EIL) and an electron transporting layer (ETL) may be stacked at an upper portion of each photoelectric conversion layer 585. Each of these layers may be a single layer or a multiple layer made of an organic material.

The common electrode 590 may be disposed on the emission layers 575, the photoelectric conversion layers 585, and the bank layer BK. The common electrode 590 may be disposed throughout the plurality of pixels PX and the plurality of photo-sensors PS in a form in which it covers the emission layers 575, the photoelectric conversion layers 585, and the bank layer BK. The common electrode 590 may include a material layer having a small work function, for example, Li, Ca, LiF/Ca, LiF/Al, Al, Mg, Ag, Pt, Pd, Ni, Au, Nd, Ir, Cr, BaF, Ba, or compounds or mixtures thereof (e.g., a mixture of Ag and Mg, etc.). In addition, the common electrode 590 may include transparent metal oxide, for example, indium-tin-oxide (ITO), indium-zinc-oxide (IZO), or zinc oxide (ZnO).

The common electrode 590 may be commonly disposed on the emission layer 575 and the photoelectric conversion layer 585, but the present invention is not limited thereto. In this case, a cathode electrode (e.g., the common electrode) of the light emitting element EL and a sensing cathode electrode of the photoelectric conversion element PD may be electrically connected to each other. For example, a common voltage line connected to the cathode electrode of the light emitting element EL may also be connected to the sensing cathode electrode of the photoelectric conversion element PD.

An encapsulation layer TFEL may be disposed on the light emitting element layer EML. The encapsulation layer TFEL may include at least one inorganic film to prevent oxygen or moisture from penetrating into each of the emission layer 575 and the photoelectric conversion layer 585. In addition, the encapsulation layer TFEL may include at least one organic film to protect each of the emission layer 575 and the photoelectric conversion layer 585 from foreign materials such as dust. For example, the encapsulation layer TFEL may be formed as a structure in which a first inorganic film 611, an organic film 612, and a second inorganic film 613 are sequentially stacked on each other. For example, each of the first inorganic film 611 and the second inorganic film 613 may be formed as a multilayer film in which one or more inorganic films of a silicon nitride layer, a silicon oxynitride layer, a silicon oxide layer, a titanium oxide layer, and an aluminum oxide layer are alternately stacked. The organic film 612 may be an organic film made of, for example, an acrylic resin, an epoxy resin, a phenolic resin, a polyamide resin, a polyimide resin, or the like.

A pressure sensing layer PRS may be disposed on the encapsulation layer TFEL. The pressure sensing layer PRS may be provided in the form of a panel or a film, and may be attached onto the encapsulation layer TFEL through a bonding layer such as a pressure sensitive adhesive (PSA). The pressure sensing layer PRS is positioned on a light emission path of a light emitting element layer EML, and may thus be transparent.

The pressure sensing layer PRS serves to sense a pressure applied to the display device 1. When the user or the like touches an upper surface of the display device 1, a pressure applying force of a touch input may be sensed by the pressure sensing layer PRS. A pressure sensing electrode of the pressure sensing layer PRS may be formed on a touch layer. In this case, the pressure sensing layer PRS may be incorporated in the display panel 10 together with the display layer 120 and the touch layer.

A window WDL may be disposed on the pressure sensing layer PRS. The window WDL may be disposed on the display device 1 to protect components of the display device 1, after a cutting process and a module process of the display cell 100 are performed. The window WDL may be made of, for example, glass or plastic.

In addition, FIG. 5 is a cross-sectional view illustrating a state in which a finger of a user touches the window WDL of the display device 1, and when a finger or the like of a user OBJ touches an upper surface of the window WDL, light output from the emission areas of the pixels PX may be reflected from the finger or the like of the user OBJ. In this case, blood flow rates according to pressures in a blood vessel of the finger or the like of the user OBJ may be different from each other. Accordingly, the blood flow rate of the blood vessel of the finger or the like of the user OBJ may be derived based on a difference in an amount of the reflected light, that is, the light incident on the photo-sensors PS. For example, the light reflected from the finger or the like of the user OBJ may be received by the photo-sensors PS to determine the blood flow rate of the blood vessel. A blood pressure of the user OBJ may be measured through the photo-sensors PS and the pressure sensing layer PRS.

Figure 6:
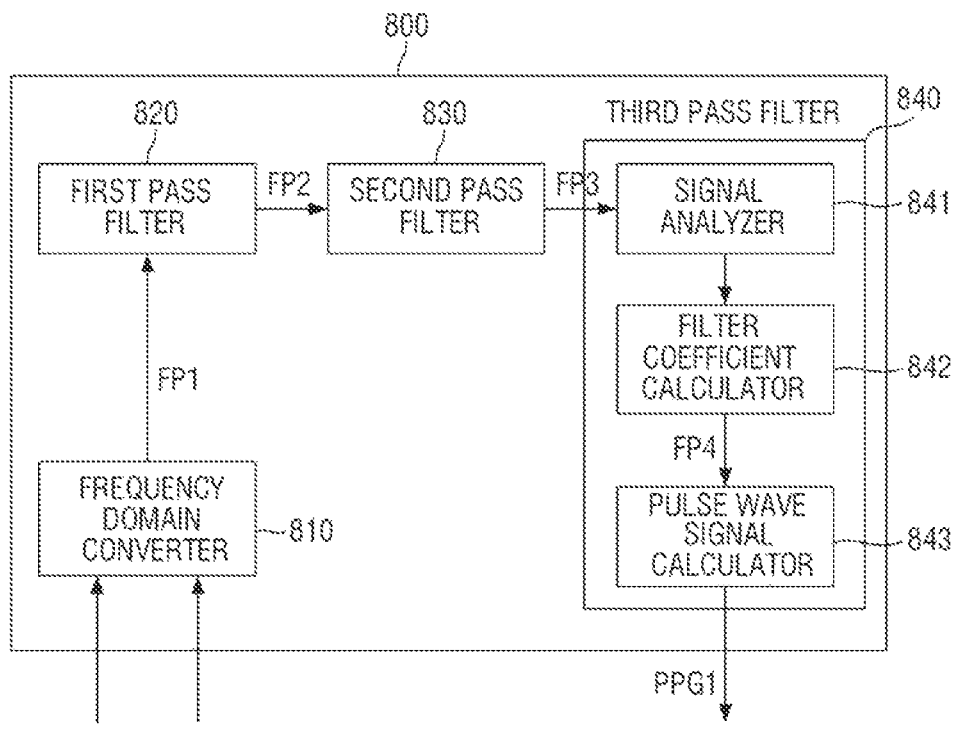
FIG. 6 is a block diagram illustrating a filter unit according to an embodiment of the present invention.

FIG. 6 is a block diagram illustrating a filter unit according to an embodiment of the present invention.

Referring to FIG. 6, the filter unit 800 includes a frequency domain converter 810, a first pass filter 820, a second pass filter 830, and a third pass filter 840.

The frequency domain converter 810 receives the pulse wave signal PPG according to a time from the pulse wave sensing circuit 50. In addition, the frequency domain converter 810 receives a pressure value according to a time from the pressure sensing circuit 40. The frequency domain converter 810 calculates a first pulse wave frequency signal FP1 based on the received pulse wave signal PPG according to a time and pressure value according to a time. The first pulse wave frequency signal FP1 may be a magnitude of the pulse wave signal PPG according to a frequency (see FIG. 11).

For example, the frequency domain converter 810 may calculate each frequency of the pulse wave signals PPG from a pulse wave signal value according to a time. The frequency domain converter 810 may calculate a pulse wave signal value of each frequency that is calculated. In addition, the frequency domain converter 810 may convert the pulse wave signal into the first pulse wave frequency signal FP1 based on the pulse wave signal value of each frequency and the pressure value according to a time. The converted first pulse wave frequency signal FP1 may include a plurality of harmonics. The plurality of harmonics may include 0th harmonics f0 (see FIG. 11) having a peak of the pulse wave signal PPG of which a frequency is 0 (direct current (DC) component), first harmonics f1 (see FIG. 11) corresponding to a first peak of the pulse wave signal PPG, second harmonics f2 (see FIG. 11) corresponding to a second peak of the pulse wave signal PPG, third harmonics f3 (see FIG. 11) corresponding to a third peak of the pulse wave signal PPG, and fourth harmonics f4 (see FIG. 11) corresponding to a fourth peak of the pulse wave signal PPG. A fast Fourier transform (FFT) method may be applied as a frequency domain conversion method of the pulse wave signal PPG.

The first pass filter 820 may receive the first pulse wave frequency signal FP1 from the frequency domain converter 810. The first pass filter 820 may block a signal of the $0^{th}$ harmonics f0 (see FIG. 11) among a plurality of frequencies of the first pulse wave frequency signal FP1. For example, the first pass filter 820 may be a low pass filter (LPF) passing a low frequency band and blocking a frequency of a high frequency or higher. For example, the first pass filter 820 may block a frequency band of the $0^{th}$ harmonics f0 (see FIG. 11) of the DC component and may pass frequency bands of the first harmonics f1 (see FIG. 11) to the fourth harmonics f4 (see FIG. 11). Accordingly, linear noise according to the DC component included in the first pulse wave frequency signal FP1 may be removed. The first pass filter 820 may block the frequency band of the $0^{th}$ harmonics f0 (see FIG. 11) to generate a second pulse wave frequency signal FP2 from which the $0^{th}$ harmonics f0 (see FIG. 11) are removed. The first pass filter 820 may output the second pulse wave frequency signal FP2 to the second pass filter 830.

The second pass filter 830 may receive the second pulse wave frequency signal FP2 from the first pass filter 820. The second pass filter 830 may extract signals of the first harmonics f1 to the third harmonics f3 among a plurality of frequencies of the second pulse wave frequency signal FP2. For example, the second pass filter 830 may be a band pass filter (BPF) passing a frequency of a specific band and blocking frequencies of the other bands. For example, the second pass filter 830 may pass only frequency bands of the first harmonics f1 to the third harmonics f3 and block the other frequency bands. Accordingly, noise of a high frequency component included in the fourth harmonics f4 of the second pulse wave frequency signal FP2 and noise of a low frequency component less than the first harmonics f1 may be removed. The second pass filter 830 may generate a third pulse wave frequency signal FP3 including the first harmonics f1 to the third harmonics f3. The second pass filter 830 may output the third pulse wave frequency signal FP3 to the third pass filter 840.

The third pass filter 840 may receive the third pulse wave frequency signal FP3 from the second pass filter 830. The third pass filter 840 may calculate a coefficient of a third transfer function H3(x) (see FIG. 17) of the third pass filter 840 and block signals other than the first harmonics f1 to the third harmonics f3 among a plurality of frequencies of the third pulse wave frequency signal FP3. The third pass filter 840 may calculate the coefficient of the third transfer function H3(x) (see FIG. 17) of the third pass filter 840 and amplify each of the first harmonics f1 to the third harmonics f3. For example, the third pass filter 840 may be a plurality of band pass filters (BPFs) passing a frequency of a specific band and blocking frequencies of the other bands.

The third pass filter 840 may generate a fourth pulse wave frequency signal FP4 including the first harmonics f1 to the third harmonics f3. The third pass filter 840 may generate a first pulse wave signal PPG1 based on the fourth pulse wave frequency signal FP4. The third pass filter 840 may output the first pulse wave signal PPG1 to the blood pressure calculation unit 900.

The third pass filter 840 includes a signal analyzer 841, a filter coefficient calculator 842, and a pulse wave signal calculator 843.

The signal analyzer 841 may receive the third pulse wave frequency signal FP3 from the second pass filter 830. The signal analyzer 841 may detect center frequencies and maximum gains in the first harmonics f1 to the third harmonics f3 of the third pulse wave frequency signal FP3. For example, the signal analyzer 841 may detect a center frequency of the first harmonics f1 and a maximum gain at the center frequency of the first harmonics f1, a center frequency of the second harmonics f2 and a maximum gain at the center frequency of the second harmonics f2, and a center frequency of the third harmonics f3 and a maximum gain at the center frequency of the third harmonics f3. In addition, the signal analyzer 841 may detect a cutoff frequency of a transfer function of the third pass filter 840. The signal analyzer 841 may output the center frequencies, the cutoff frequencies, and the maximum gains detected in the third pulse wave frequency signal FP3 to the filter coefficient calculator 842.

The filter coefficient calculator 842 may receive the center frequencies, the cutoff frequencies, and the maximum gains detected in the third pulse wave frequency signal FP3 from the signal analyzer 841. The filter coefficient calculator 842 may calculate a coefficient of the transfer function based on detected values of the third pulse wave frequency signal FP3. Specifically, the filter coefficient calculator 842 may calculate the coefficient of the transfer function of the third pass filter 840 so that the third pass filter 840 becomes a plurality of band pass filters (BPFs). Accordingly, the third pass filter 840 may block signals other than the first harmonics f1 to the third harmonics f3 among the plurality of frequencies of the third pulse wave frequency signal FP3. A detailed description of a first transfer function LPF will be provided later with reference to FIGS. 7 to 21.

The pulse wave signal calculator 843 may receive the set coefficient of the third transfer function H3($x$) (see FIG. 17) from the filter coefficient calculator 842. The pulse wave signal calculator 843 may generate the fourth pulse wave frequency signal FP4 through the third transfer function H3($x$) (see FIG. 17) to the third pulse wave frequency signal FP3. The fourth pulse wave frequency signal FP4 may be a signal in which noise components for each user are removed and gains of the first harmonics f1 to f3 are amplified. In addition, the pulse wave signal calculator 843 may generate the first pulse wave signal PPG1 based on the fourth pulse wave frequency signal FP4. The pulse wave signal calculator 843 may output the first pulse wave signal PPG1 to the blood pressure calculation unit 900.

According to an embodiment of the present invention illustrated in FIG. 6, when blood pressure calculation is inaccurate due to the presence of different noise components for each user in the pulse wave signal PPG, the filter unit 800 may increase accuracy of blood pressure calculation by extracting and blocking the noise components for each user.

Figure 8:
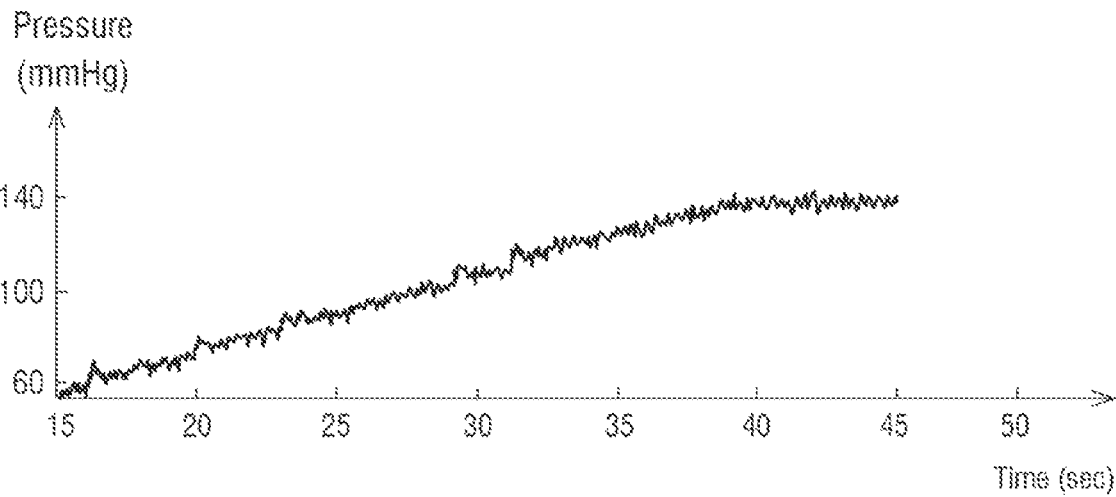
FIG. 8 is a graph illustrating a pressure measurement value according to a pressure applying time.
Figure 9:
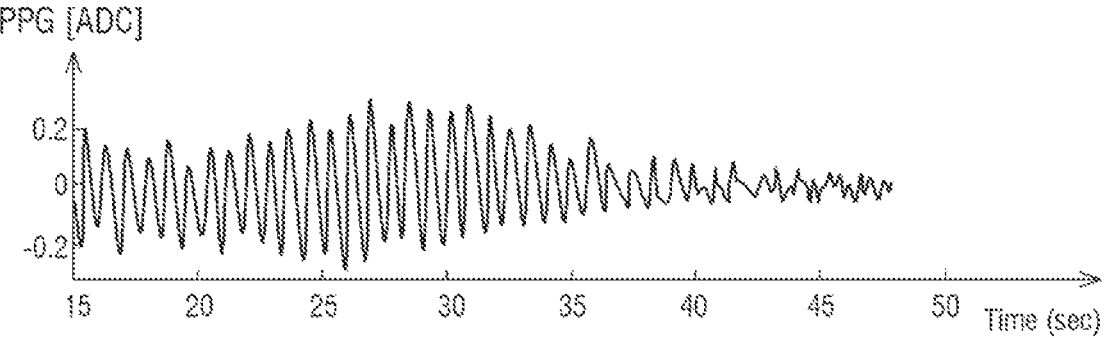
FIG. 9 is a graph illustrating a pulse wave signal according to a pressure applying time.
Figure 10:
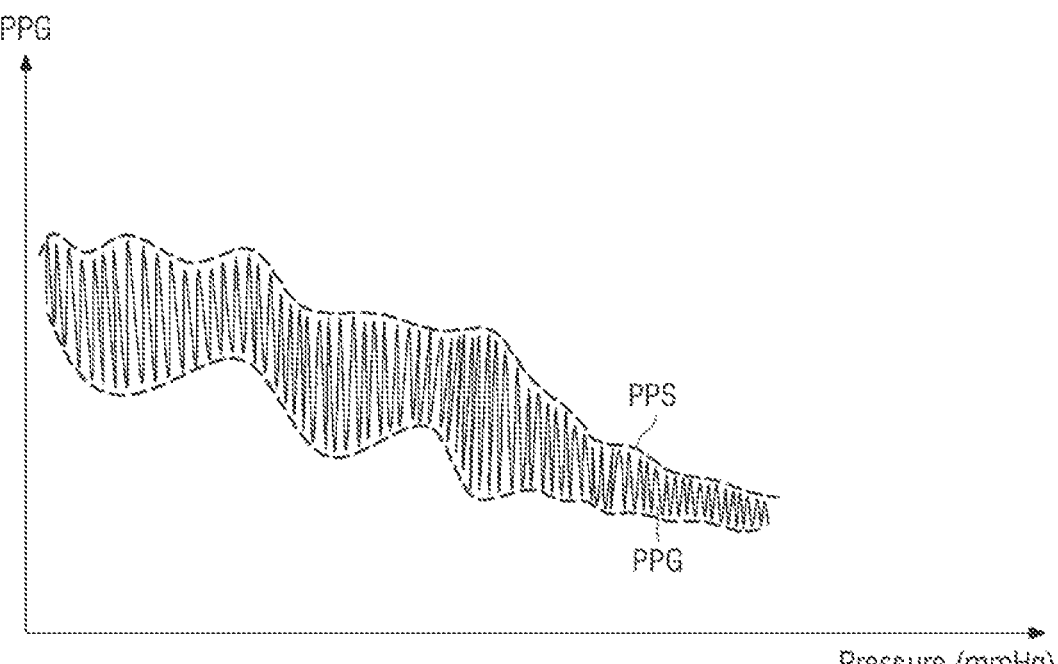
FIG. 10 is a graph illustrating a pulse wave signal according to a pressure.
Figure 11:
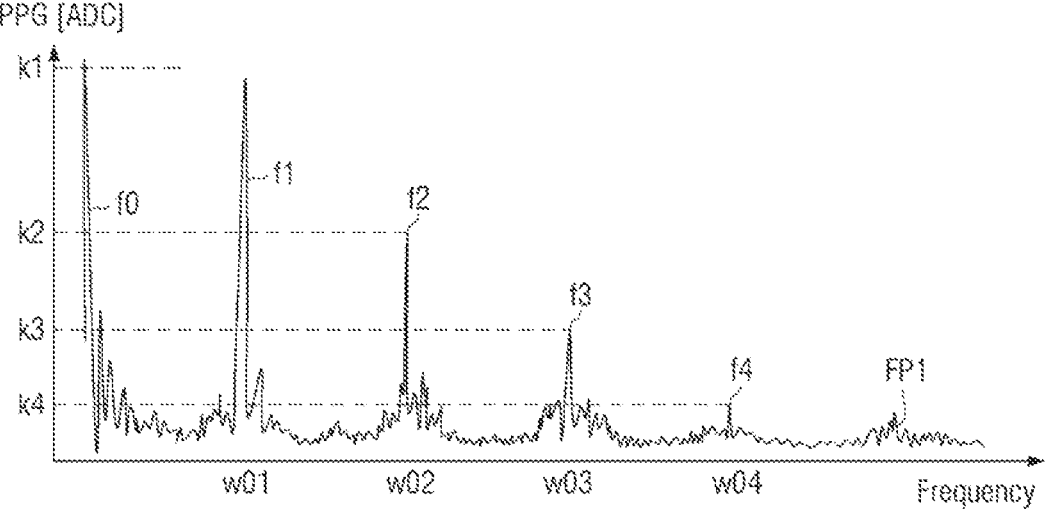
FIG. 11 is a graph illustrating a pulse wave frequency signal according to a frequency.
Figure 12:
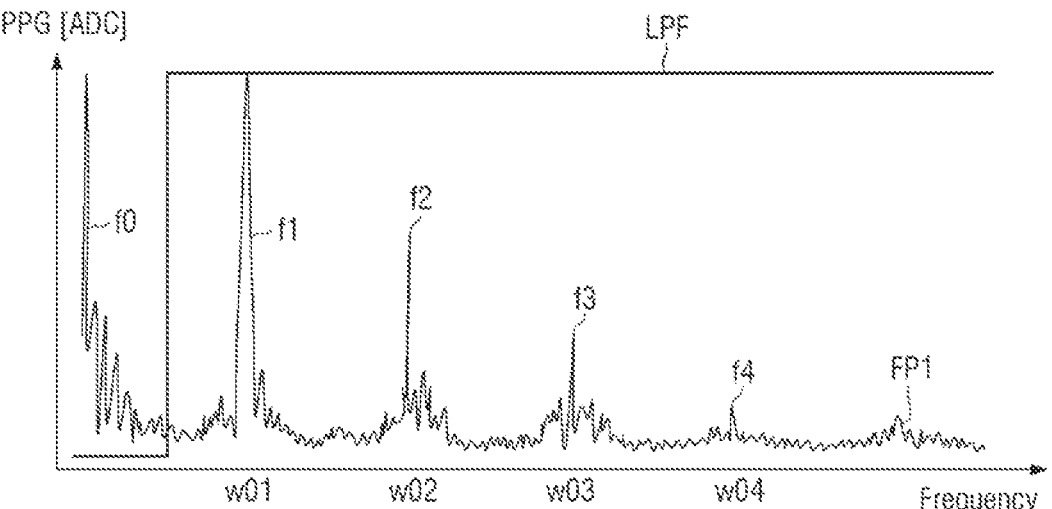
FIG. 12 is a graph illustrating a pulse wave frequency signal and a first transfer function according to a frequency.
Figure 13:
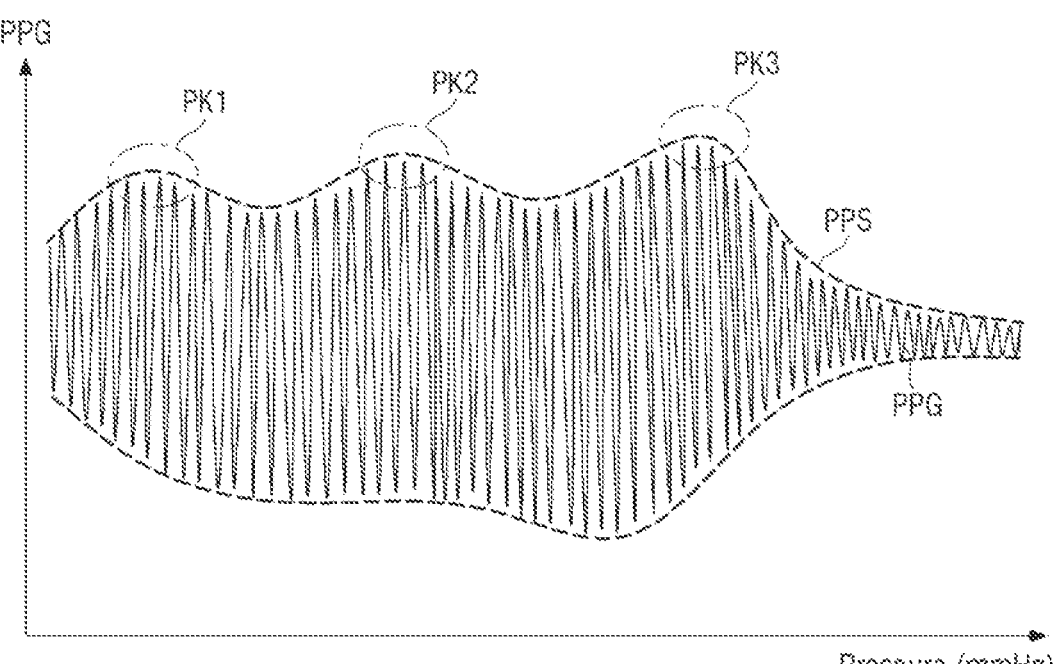
FIG. 13 is a graph illustrating a pulse wave signal according to a pressure.
Figure 14:
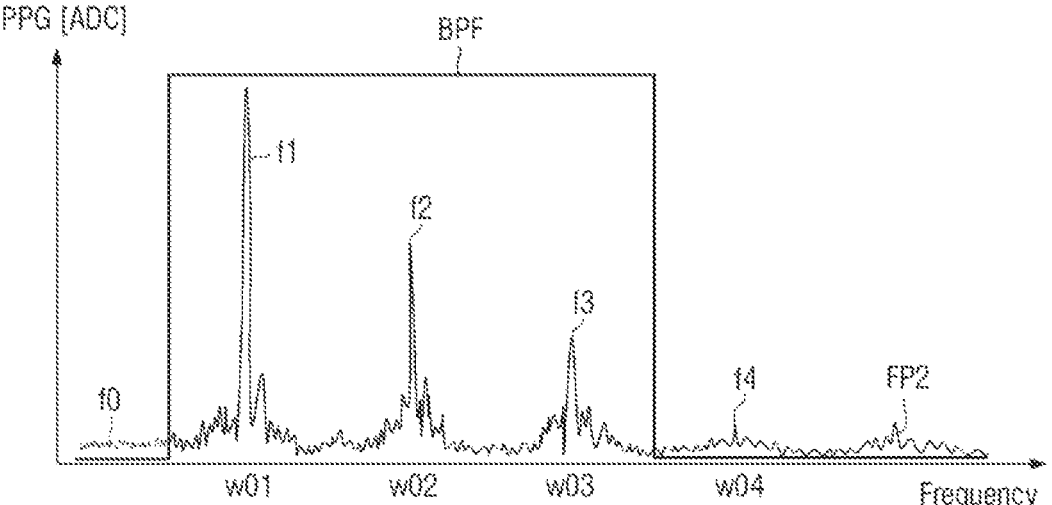
FIG. 14 is a graph illustrating a pulse wave frequency signal and a second transfer function according to a frequency.
Figure 15:
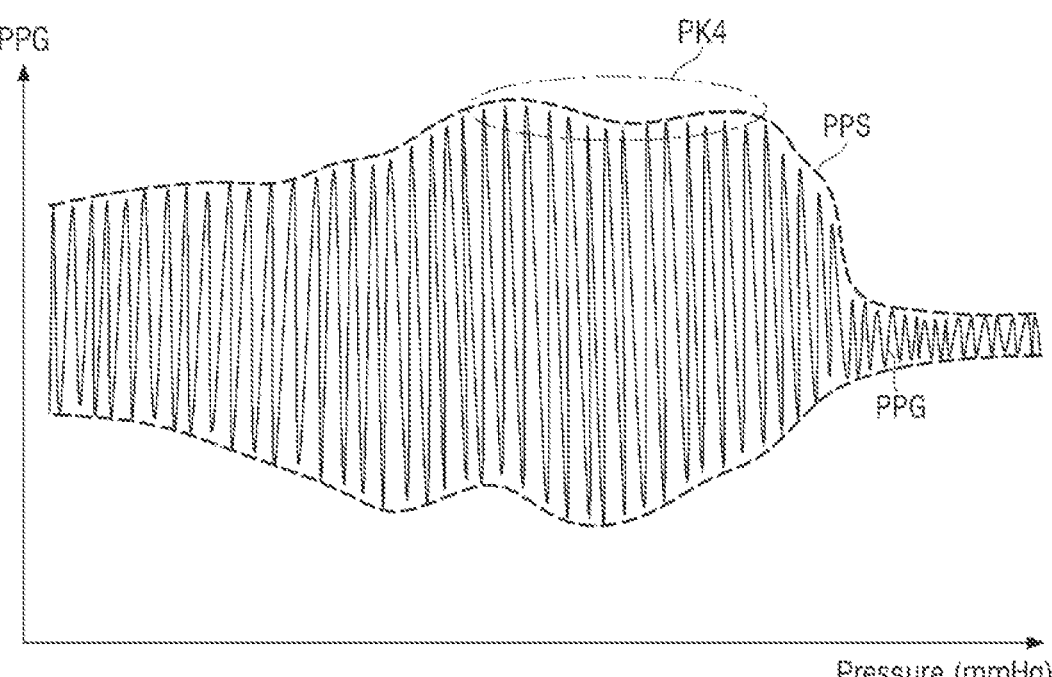
FIG. 15 is a graph illustrating a pulse wave signal according to a pressure.
Figure 17:
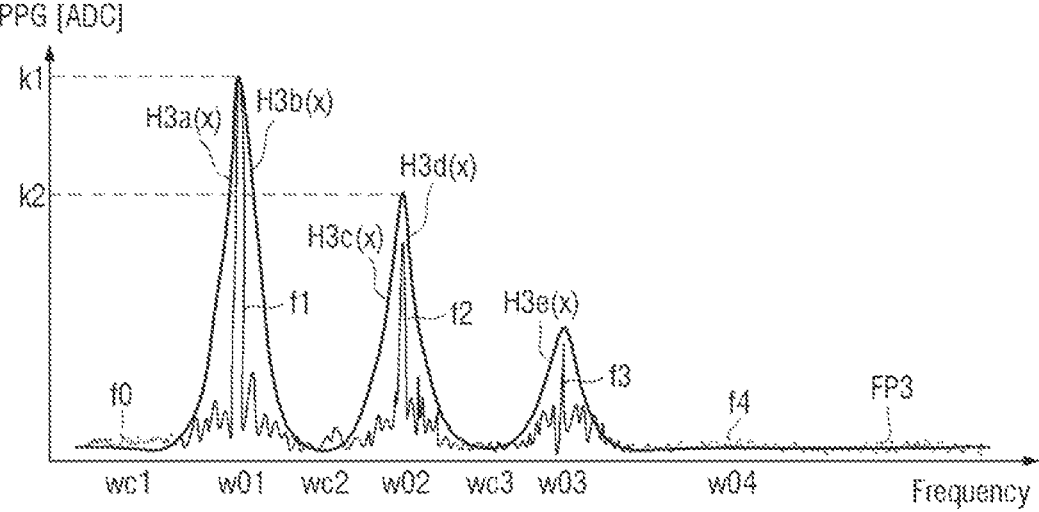
FIG. 17 is a graph illustrating a pulse wave frequency signal and a third transfer function according to a frequency.
Figure 19:
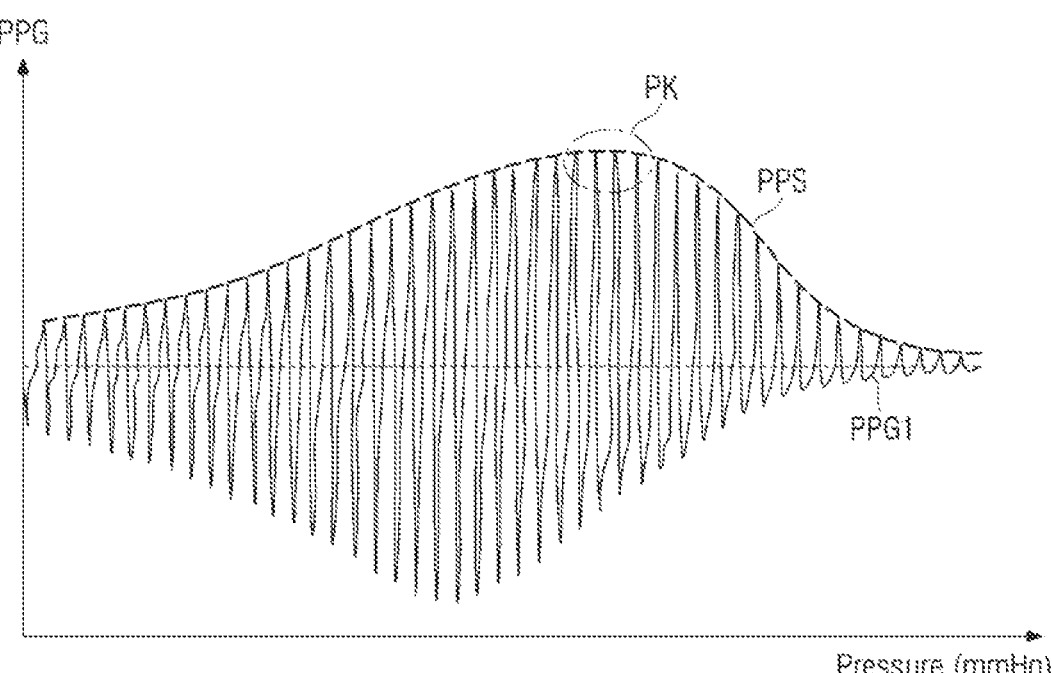
FIG. 19 is a graph illustrating a pulse wave signal according to a pressure.
Figure 20:
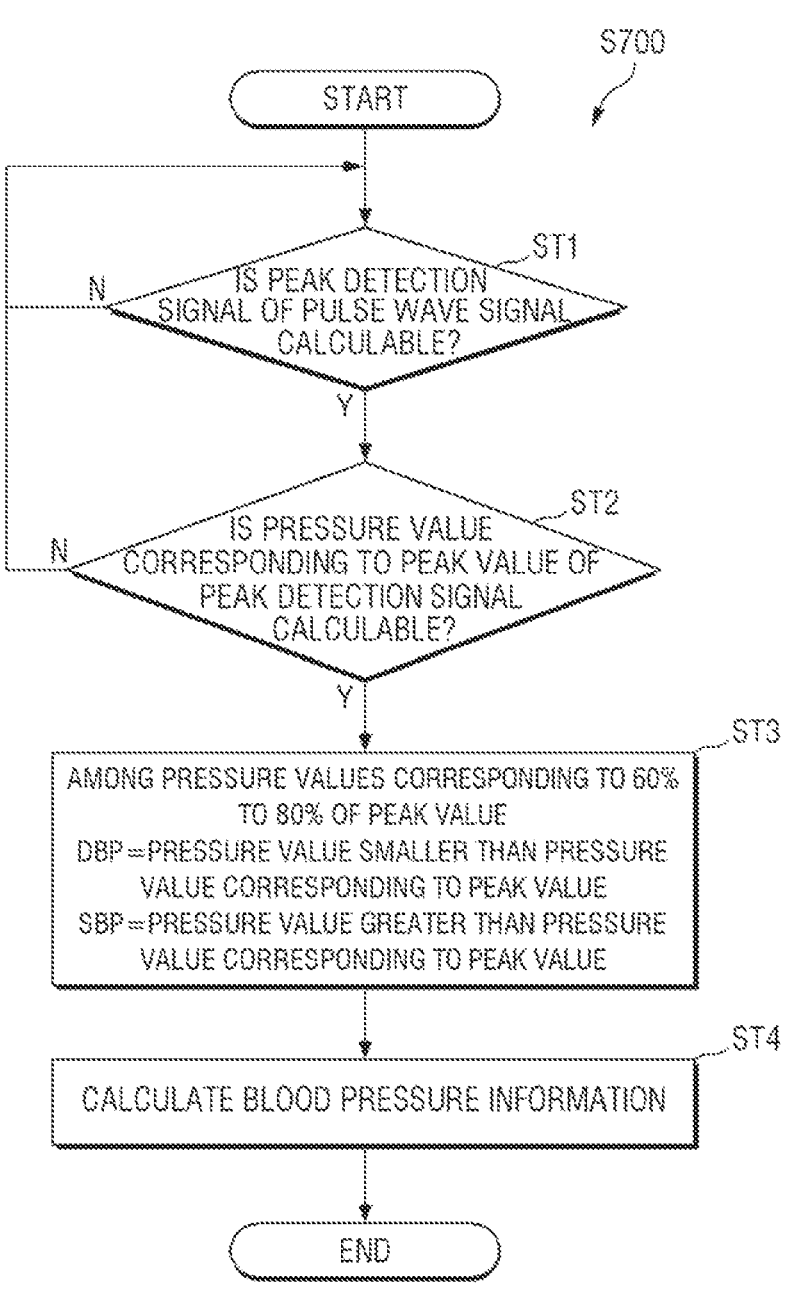
FIG. 20 is a flowchart illustrating a method of calculating a blood pressure using a generated pulse wave signal.
Figure 21:
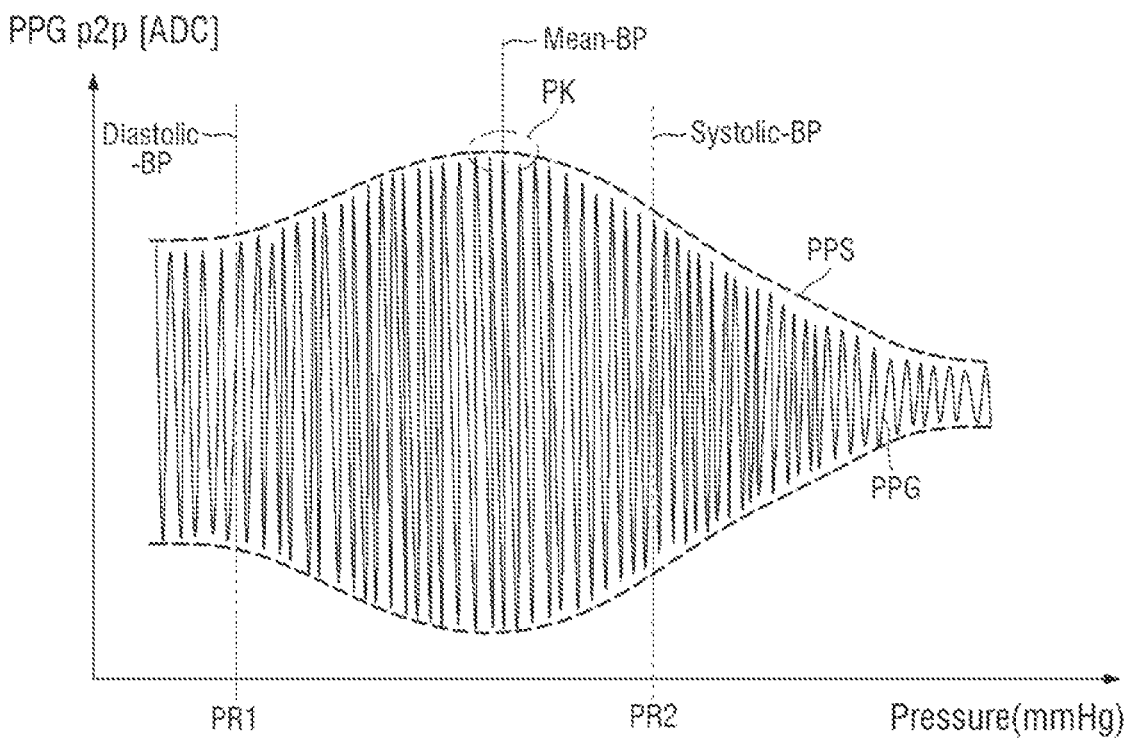
FIG. 21 is a graph illustrating the method of calculating a blood pressure using a generated pulse wave signal.

FIG. 7 is a flowchart illustrating a blood pressure measurement method using the display device according to an embodiment of the present invention. FIG. 8 is a graph illustrating a pressure measurement value according to a pressure applying time. FIG. 9 is a graph illustrating a pulse wave signal according to a pressure applying time. FIG. 10 is a graph illustrating a pulse wave signal according to a pressure. FIG. 11 is a graph illustrating a pulse wave frequency signal according to a frequency. FIG. 12 is a graph illustrating a pulse wave frequency signal and a first transfer function according to a frequency. FIG. 13 is a graph illustrating a pulse wave signal according to a pressure. FIG. 14 is a graph illustrating a pulse wave frequency signal and a second transfer function according to a frequency. FIG. 15 is a graph illustrating a pulse wave signal according to a pressure. FIG. 16 is a flowchart illustrating a method of calculating a coefficient of a 3$a$-th transfer function according to an embodiment of the present invention. FIG. 17 is a graph illustrating a pulse wave frequency signal and a third transfer function according to a frequency. FIG. 18 is a flowchart illustrating a method of calculating a coefficient of a 3$b$-th transfer function according to an embodiment of the present invention FIG. 19 is a graph illustrating a pulse wave signal according to a pressure. FIG. 20 is a flowchart illustrating a method of calculating a blood pressure using a generated pulse wave signal. FIG. 21 is a graph illustrating the method of calculating a blood pressure using a generated pulse wave signal.

A blood pressure measurement method using the display device 1 will be described with reference to FIGS. 7 to 21.

Referring to FIG. 7, first, the pressure sensing circuit 40 measures a pressure measurement value according to a pressure applying time, and the pulse wave sensing circuit 50 measures a pulse wave signal PPG value according to a pressure applying time (S100).

Referring further to FIGS. 8 to 10, the user may apply pressure to a position where the pressure sensor is disposed, and the pressure sensor may measure a pressure measurement value of the pressure applied by the user. A method of generating the pulse wave signal PPG will be described in detail. For example, in a process in which the user touches the display device 1 with his or her finger, the pressure measurement value measured by the pressure sensor may gradually increase over time to reach a maximum value. When the pressure measurement value (e.g., a touch pressure) increases, a blood vessel may be constricted, such that a blood flow rate may be decreased or become 0.

In addition, to generate the pulse wave signal PPG, pulse wave information according to a time is also used together with the pressure data. During systole of the heart, blood ejected from the left ventricle of the heart moves to peripheral tissues, such that a blood volume in the arterial side increases. In addition, during the systole of the heart, red blood cells carry more oxyhemoglobin to the peripheral tissues. During diastole of the heart, there is partial suction of blood from the peripheral tissues towards the heart. In this case, when a peripheral blood vessel is irradiated with light emitted from a display pixel, the emitted light may be absorbed by the peripheral tissue. Absorbance is dependent on a hematocrit and a blood volume. The absorbance may have a maximum value during the systole of the heart and a minimum value during the diastole of the heart. Since the absorbance is in inverse proportion to an amount of light incident on the photo-sensor PS, absorbance at a corresponding point in time may be estimated through light reception data of the amount of light incident on the photo-sensor PS, and accordingly, as illustrated in FIG. 9, a pulse wave signal PPG value according to a time may be generated.

The pulse wave information according to a time reflects the maximum value of the absorbance during the systole of the heart, and reflects the minimum value of the absorbance during the diastole of the heart. In addition, the pulse wave vibrates according to a heartbeat cycle. Accordingly, the pulse wave information may reflect a change in blood pressure according to a heartbeat. Accordingly, the pulse wave sensing circuit 50 may measure the pulse wave signal PPG value according to the pressure applying time.

Accordingly, referring to FIG. 10, the main processor 710 may generate the pulse wave signal PPG through the pressure measurement value and the pulse wave signal PPG value. However, the pulse wave signal PPG vibrates according to the heartbeat cycle, and may thus reflect a change in blood pressure according to the heartbeat. In this case, since each user has a different heartbeat cycle and the pulse wave signal PPG changes according to a change in the heartbeat cycle, each user may have a pulse wave signal PPG of a different harmonics component. In addition, a noise component due to tissues, skins, blood vessels, and the like, may be included in the pulse wave signal PPG.

In addition, as described later, the main processor 710 may generate a peak detection signal PPS using peaks of the pulse wave signal PPG. The peak detection signal PPS is defined as a signal corresponding to each peak value of one cycle of the pulse wave signal PPG. For example, the peak detection signal PPS (see FIG. 10) may have one or more peak values. Accordingly, when different noise components for each user are included in the pulse wave signal PPG, the peak detection signal PPS may have a plurality of peak values, such that blood pressure calculation may be inaccurate. Accordingly, the noise components for each user need to be extracted and blocked from the pulse wave signal PPG.

Next, the filter unit 800 generates the first pulse wave frequency signal FP1 converted into a magnitude of the pulse wave signal PPG according to a frequency having a fundamental wave component and a harmonics component based on the measurement values (S200).

The filter unit 800 receives the pulse wave signal PPG according to a time from the pulse wave sensing circuit 50. In addition, the filter unit 800 receives the pressure value according to a time from the pressure sensing circuit 40. The filter unit 800 calculates the first pulse wave frequency signal FP1 based on the received pulse wave signal PPG according to a time and pressure value according to a time. The first pulse wave frequency signal FP1 may be a magnitude of the pulse wave signal PPG according to a frequency. Specifically, the filter unit 800 may calculate each frequency of the pulse wave signals PPG from the pulse wave signal value according to a time. The filter unit 800 may calculate the pulse wave signal value of each frequency that is calculated. In addition, the filter unit 800 may convert the pulse wave signal into the first pulse wave frequency signal FP1 based on the pulse wave signal value of each frequency and the pressure value according to a time. A fast Fourier transform (FFT) method may be applied as a frequency domain conversion method of the pulse wave signal (PPG).

Referring to FIG. 11, the first pulse wave frequency signal FP1 may include a plurality of harmonics. For example, the first pulse wave frequency signal FP1 may include the $0^{th}$ harmonics f0 having the peak of the pulse wave signal PPG of which the center frequency is 0 (DC component). In addition, the first pulse wave frequency signal FP1 may include the first harmonics f1 corresponding to the first peak of the first pulse wave frequency signal FP1. The first harmonics f1 may have a first maximum gain k1 at a first center frequency w01. In addition, the first pulse wave frequency signal FP1 may include the second harmonics f2 corresponding to the second peak of the first pulse wave frequency signal FP1. The second harmonics f2 may have a second maximum gain k2 at a second center frequency w02. In addition, the first pulse wave frequency signal FP1 may include the third harmonics f3 corresponding to the third peak of the first pulse wave frequency signal FP1. The third harmonics f3 may have a third maximum gain k3 at a third center frequency w03. In addition, the first pulse wave frequency signal FP1 may include the fourth harmonics f4 corresponding to the fourth peak of the first pulse wave frequency signal FP1. The fourth harmonics f4 may have a fourth maximum gain k4 at a fourth center frequency.

Next, the filter unit 800 generates the second pulse wave frequency signal FP2 from which the $0^{th}$ harmonics f0 are removed by blocking noise of a fundamental wave component of the first pulse wave frequency signal FP1 (S300).

The first pass filter 820 may receive the first pulse wave frequency signal FP1 from the frequency domain converter 810. The first pass filter 820 may block the signal of the $0^{th}$ harmonics f0 among the plurality of frequencies of the first pulse wave frequency signal FP1. For example, the first pass filter 820 may be a low pass filter (LPF) passing a low frequency band and blocking a frequency of a high frequency or higher.

Referring to FIG. 12, the first pass filter 820 may have a first transfer function LPF. A cutoff frequency of the first transfer function LPF may be set to a frequency smaller than the first center frequency w01. Accordingly, the first transfer function LPF may block a $0^{th}$ harmonics f0 component having a DC component, and may pass a pulse wave frequency signal of the first harmonics f1 or more. Accordingly, linear noise according to the DC component included in the first pulse wave frequency signal FP1 may be removed.

For example, FIG. 10 illustrates a pulse wave signal PPG including linear noise according to a DC component. FIG. 13 illustrates a pulse wave signal PPG from which the linear noise according to the DC component is removed. In FIG. 13, the noise according to the DC component is removed from the pulse wave signal PPG of FIG. 10, such that the pulse wave signal PPG may have a first peak PK1 to a third peak PK3. The first pass filter 820 may block the frequency band of the $0^{th}$ harmonics f0 to generate the second pulse wave frequency signal FP2 from which the $0^{th}$ harmonics f0 are removed (see FP2 in FIG. 14).

Next, the filter unit 800 generates the third pulse wave frequency signal FP3 from which the fourth harmonics f4 are removed by blocking a high-frequency noise component of the second pulse wave frequency signal FP2 (S400).

The second pass filter 830 may receive the second pulse wave frequency signal FP2 from the frequency domain converter 810. The second pass filter 830 may extract signals of the first harmonics f1 to the third harmonics f3 among a plurality of frequencies of the second pulse wave frequency signal FP2. For example, the second pass filter 830 may be a band pass filter (BPF) passing a frequency of a specific band and blocking frequencies of the other bands.

Referring further to FIG. 14, the second pass filter 830 may have a second transfer function. A cutoff frequency of the second transfer function may be set to a frequency between the first harmonics f1 and the $0^{th}$ harmonics f0 and a frequency between the third harmonics f3 and the fourth harmonics f4. Accordingly, the second transfer function may pass only frequency bands of the first harmonics f1 to the third harmonics f3 and block the other frequency bands. Accordingly, noise of a high frequency component included in the fourth harmonics f4 of the second pulse wave frequency signal FP2 and noise of a low frequency component less than the first harmonics f1 may be removed. Specifically, FIG. 15 illustrates a pulse wave signal PPG from which noise of a high frequency component is removed according to the second transfer function. As in a case of FIG. 15, the noise of the high frequency component is removed from the second pulse wave frequency signal FP2, such that the pulse wave signal PPG may have one fourth peak. The second pass filter 830 may generate the third pulse wave frequency signal FP3 by blocking the high-frequency noise component (see FP3 of FIG. 17).

Next, a coefficient of the third transfer function H3(x) is calculated based on center frequencies and maximum gains of the first harmonics f1 to the third harmonics f3 of the third pulse wave frequency signal FP3 (S500).

The third pass filter 840 may receive the third pulse wave frequency signal FP3 from the second pass filter 830. The third pass filter 840 may calculate the coefficient of the third transfer function H3(x) of the third pass filter 840 and block signals other than the first harmonics f1 to the third harmonies f3 among the plurality of frequencies of the third pulse wave frequency signal FP3. The third pass filter 840 may calculate the coefficient of the third transfer function H3(x) of the third pass filter 840 and amplify each of the first harmonics f1 to the third harmonics f3.

The third transfer function H3(x) may be a plurality of band pass filters (BPFs) passing a frequency of a specific band and blocking frequencies of the other bands. The third transfer function H3(x) may include a 3a-th transfer function H3a(x) of a section from a first cutoff frequency wc1 to the first center frequency w01, a 3b-th transfer function H3b(x)

of a section from the first center frequency w01 to a second cutoff frequency wc2, a 3c-th transfer function H3c(x) of a section from the second cutoff frequency wc2 to the second center frequency w02, a 3d-th transfer function H3d(x) of a section from the second center frequency w02 to a third cutoff frequency wc3, and the like. A method of calculating a coefficient of the 3a-th transfer function H3a(x) will be described with further reference to FIGS. 16 and 17.

Referring further to FIGS. 16 and 17, first, the third pass filter 840 detects the first center frequency w01 and the first maximum gain k1 of the first harmonics f1 of the third pulse wave frequency signal FP3 (S510).

The third pass filter 840 may receive the third pulse wave frequency signal FP3 from the second pass filter 830. The third pass filter 840 may detect the center frequencies and the maximum gains in the first harmonics f1 to the third harmonics f3 of the third pulse wave frequency signal FP3. For example, the third pass filter 840 may detect the first center frequency w01 and the first maximum gain k1 of the first harmonics f1.

FIG. 16 illustrates that the third pass filter 840 detects the first center frequency w01 and the first maximum gain k1 of the first harmonics f1, but the present invention is not limited thereto, and the third pass filter 840 may also detect the second center frequency w02 and the second maximum gain k2 of the second harmonics f2 and the third center frequency w03 and the third maximum gain k3 of the third harmonics f3.

Second, the third pass filter 840 calculates the first cutoff frequency wc1 corresponding to a half of the first center frequency w01 of the third pulse wave frequency signal FP3 (S520).

The third pass filter 840 may detect a cutoff frequency of the 3a-th transfer function H3a(x) of the third pass filter 840. For example, a frequency corresponding to the half of the first center frequency w01 may be detected as the cutoff frequency of the 3a-th transfer function H3a(x).

FIGS. 16 and 17 illustrate that the third pass filter 840 detects the first cutoff frequency wc1, but the present invention is not limited thereto, and the third pass filter 840 may also detect the second cutoff frequency wc2 and the third cutoff frequency wc3. A description thereof will be provided later.

Third, the third pass filter 840 calculates a coefficient of the 3a-th transfer function H3a(x) in the section from the first cutoff frequency wc1 to the first center frequency w01 (S530).

The 3a-th transfer function H3a(x) may block the third pulse wave frequency signal FP3 at the first cutoff frequency wc1. For example, the 3a-th transfer function H3a(x) may have a gain of 0 at the first cutoff frequency wc1. In addition, the 3a-th transfer function H3a(x) may have a maximum gain at the first center frequency w01. For example, the 3a-th transfer function H3a(x) may have a gain corresponding to a first maximum gain k1 value at the first center frequency w01. In addition, the 3a-th transfer function H3a(x) may have a form of a downward convex polynomial function. For example, the 3a-th transfer function H3a(x) may have a form of a polynomial function of a second order or higher. The coefficient of the 3a-th transfer function H3a(x) may be calculated to have the first center frequency w01, the first maximum gain k1, the first cutoff frequency wc1, and a gain of 0. That is, the 3a-th transfer function H3a(x) may be calculated by Equation 1.

$$H3a(x) = \frac{k}{w_{01}^N - w_{c1}^N} x^N + \frac{-kw_{c1}^N}{w_{01}^N - w_{c1}^N} \qquad \text{[Equation 1]}$$

Here, $W_{01}$ is the first center frequency w01, Wc is the first cutoff frequency wc1, k is the first maximum gain k1, N is a natural number of 2 or more, x is an input pulse wave frequency signal, and H3a(x) is the 3a-th transfer function H3a(x). Accordingly, the third pass filter 840 may amplify the first harmonics f1 of the third pulse wave frequency signal FP3 and block frequency signals smaller than the first harmonics f1.

A method of calculating a coefficient of the 3b-th transfer function H3b(x) will be described with further reference to FIG. 18.

First, the first center frequency w01 and the first maximum gain k1 of the first harmonics f1 and the second center frequency w02 of the second harmonics f2 of the third pulse wave frequency signal FP3 are detected (S511). The second center frequency w02, the first center frequency w01, and the first maximum gain k1 are substantially the same as in S510 of FIG. 16, and a description thereof will thus be omitted to prevent redundant descriptions.

Second, the second cutoff frequency wc2 corresponding to an intermediate value between the first center frequency w01 and the second center frequency w02 of the third pulse wave frequency signal FP3 is calculated (S521). The third pass filter 840 may detect a cutoff frequency of the 3b-th transfer function H3b(x) of the third pass filter 840. For example, the second cutoff frequency wc2 may be a frequency corresponding to the intermediate value between the first center frequency w01 and the second center frequency w02.

Third, the coefficient of the 3b-th transfer function H3b(x) is calculated in the section from the first center frequency w01 to the second cutoff frequency wc2 (S531).

The 3b-th transfer function H3b(x) may have a form of a downward convex polynomial function. For example, the 3b-th transfer function H3b(x) may have a form of a polynomial function of a second order or higher. The coefficient of the 3b-th transfer function H3b(x) may be calculated to have the first center frequency w01, the first maximum gain k1, the second cutoff frequency wc2, and a gain of 0. That is, the 3b-th transfer function H3b(x) may be calculated by Equation 2.

$$H3b(x) = \frac{-k}{w_{c2}^N - w_{01}^N} x^N + \frac{-kw_{01}^N}{w_{c2}^N - w_{01}^N} \qquad \text{[Equation 2]}$$

Here, $W_{01}$ is the first center frequency w01, Wc is the first cutoff frequency wc1, k is the first maximum gain k1, N is a natural number of 2 or more, x is an input pulse wave frequency signal, and H3b(x) is the 3b-th transfer function H3b(x).

Accordingly, the third pass filter 840 may amplify the first harmonics f1 of the third pulse wave frequency signal FP3 and block frequency signals smaller than the first harmonics f1.

Methods of calculating coefficients of the 3c-th transfer function H3c(x), the 3d-th transfer function H3d(x), a 3e-th transfer function H3e (x), and the like, may be substantially the same as the methods of calculating the coefficients of the 3a-th transfer function H3a(x) and the 3b-th transfer function H3b(x) as illustrated in FIGS. 16 to 18.

Accordingly, according to an embodiment of the present invention with reference to FIGS. 16 to 18, the fourth pulse wave frequency signal FP4 may be a signal in which noise components for each user are removed and gains of the first harmonics f1 to f3 are amplified.

Referring to FIG. 7 again, the third pass filter 840 generates the fourth pulse wave frequency signal FP4 by blocking noise components of the first harmonics f1 to the third harmonics f3 of the third pulse wave frequency signal FP3 based on the third transfer function H3($x$), and generates the first pulse wave signal PPG1 based on the fourth pulse wave frequency signal FP4 (S600). For example, a noise component of the first harmonics f1 in a section from the first cutoff frequency wc1 to the first center frequency w01 may be blocked.

Referring further to FIG. 19, the third pass filter 840 may generate the first pulse wave signal PPG1 based on the fourth pulse wave frequency signal FP4. In the first pulse wave signal PPG1, different noise components for each user may be blocked through the filter unit 800.

Finally, blood pressure information is calculated based on the first pulse wave signal PPG1 (S700).

Referring to FIGS. 20 and 21, first, the main processor 710 determines whether or not the peak detection signal PPS may be calculated based on the first pulse wave signal PPG1 (ST1).

The main processor 710 may generate the peak detection signal PPS using peaks of the first pulse wave signal PPG1. The peak detection signal PPS may be a signal corresponding to each peak value of one cycle of the first pulse wave signal PPG1. For example, the first pulse wave signal PPG1 may have one or more peak values. The main processor 710 may calculate the peak detection signal PPS including points corresponding to the peak values of the first pulse wave signal PPG1.

Next, the main processor 710 determines whether or not a pressure value corresponding to the peak value PK of the peak detection signal PPS may be calculated (ST2).

When a peak of the peak detection signal PPS exists, the main processor 710 may calculate a pressure value corresponding to the peak value PK of the peak detection signal PPS.

Next, the main processor 710 calculates a systolic blood pressure SBP, a diastolic blood pressure DBP, and the like, based on the peak value PK of the peak detection signal PPS (ST3), and calculates blood pressure information (ST4).

The main processor 710 may calculate the diastolic blood pressure DBP lower than the pressure value, the systolic blood pressure SBP higher than the pressure value, and a mean blood pressure according to the pressure value. For example, the main processor 710 may calculate pressure values corresponding to values corresponding to about 60% to about 80% of the peak value PK. The main processor 710 may calculate a pressure value smaller than a pressure value corresponding to the peak value PK among the pressure values as a first pressure value PR1. In addition, the main processor 710 may calculate the first pressure value PR1 as the diastolic blood pressure DBP. In addition, the main processor 710 may calculate a pressure value greater than the pressure value corresponding to the peak value PK among the pressure values as a second pressure value PR2. In addition, the main processor 710 may calculate the second pressure value PR2 as the systolic blood pressure SBP.

In a case of the embodiment, the pulse wave signal PPG vibrates according to the heartbeat cycle, and may thus reflect a change in blood pressure according to the heartbeat. In this case, since each user has a different heartbeat cycle and the pulse wave signal changes according to a change in the heartbeat cycle, each user may have a pulse wave signal of a different harmonics component. In addition, a noise component due to tissues, skins, blood vessels, and the like, may be included in the pulse wave signal.

Accordingly, since different noise components for each user may be included in the pulse wave signal, blood pressure calculation may be inaccurate. In this case, the third pass filter extracts and blocks noise components for each user from the pulse wave signal, such that the blood pressure may be accurately calculated.

Figure 22:
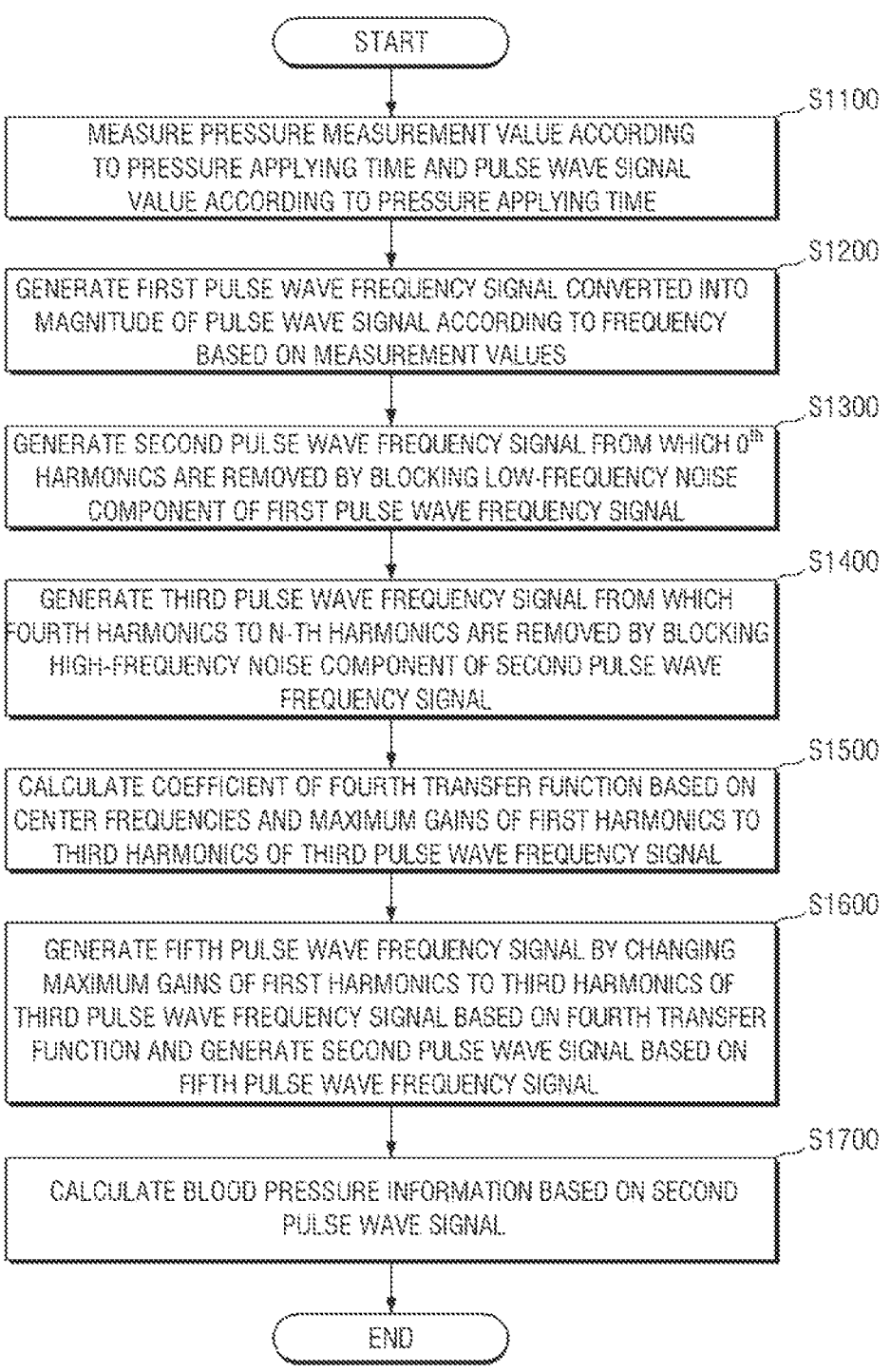
FIG. 22 is a flowchart illustrating a blood pressure measurement method using a display device according to an embodiment of the present invention.
Figure 24:
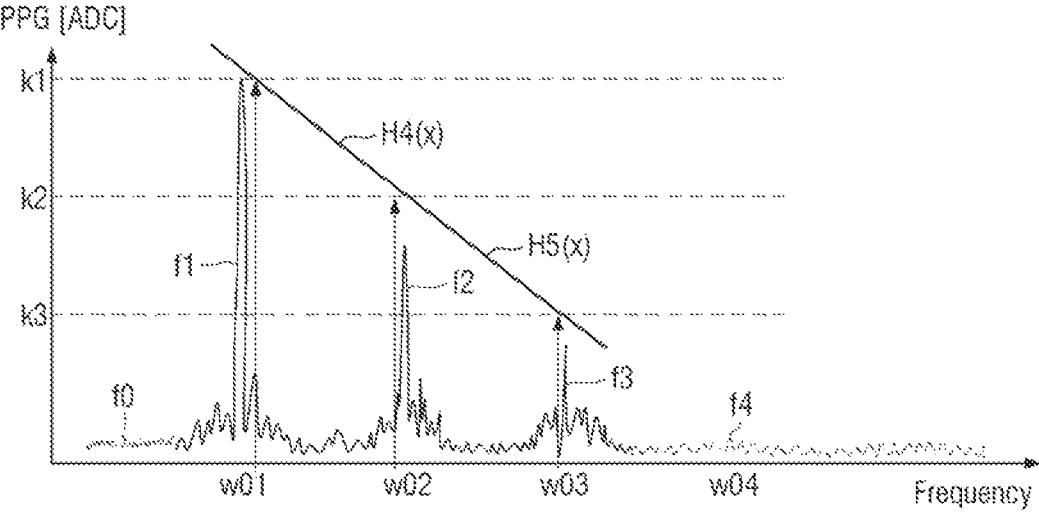
FIG. 24 is a graph illustrating a pulse wave frequency signal and a fourth transfer function according to an embodiment of the present invention.
Figure 25:
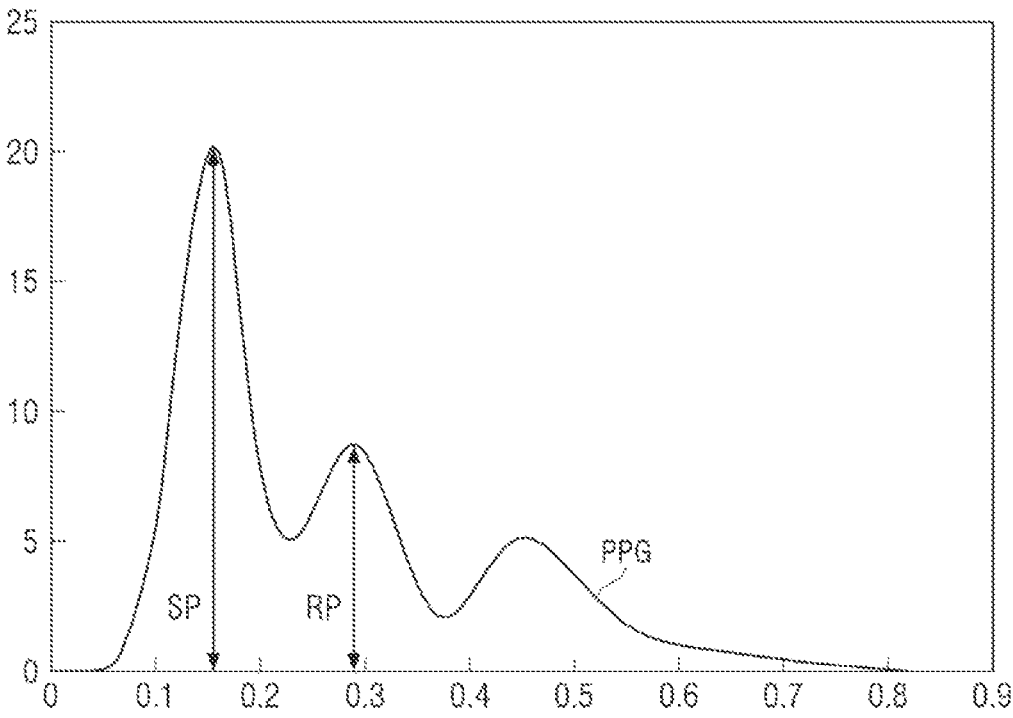
FIGS. 25, 26 and 27 are enlarged graphs of waveforms of the pulse wave signal illustrated in FIG. 21.
Figure 26:
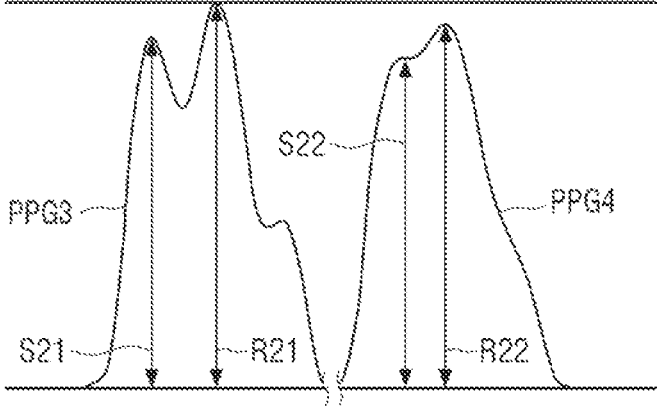
Figure 27:
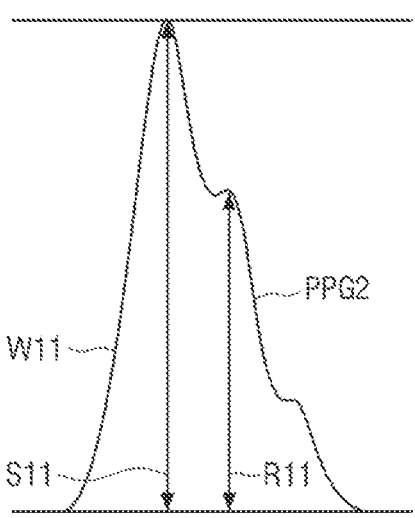
Figure 28:
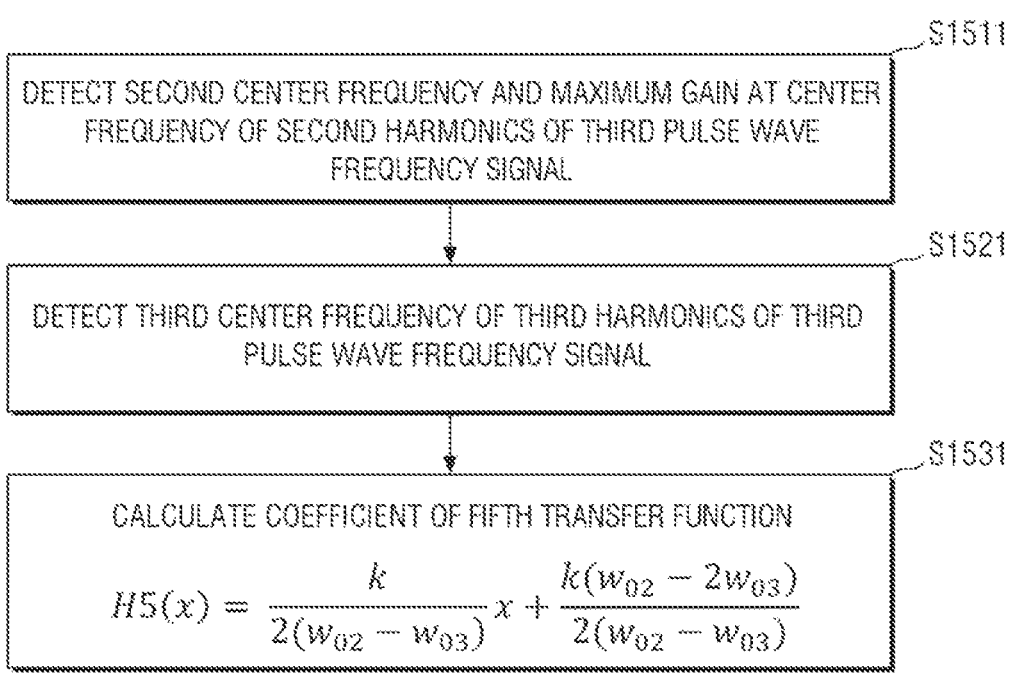
FIG. 28 is a flowchart illustrating a method of calculating a coefficient of a fourth transfer function according to an embodiment of the present invention.
Figure 29:
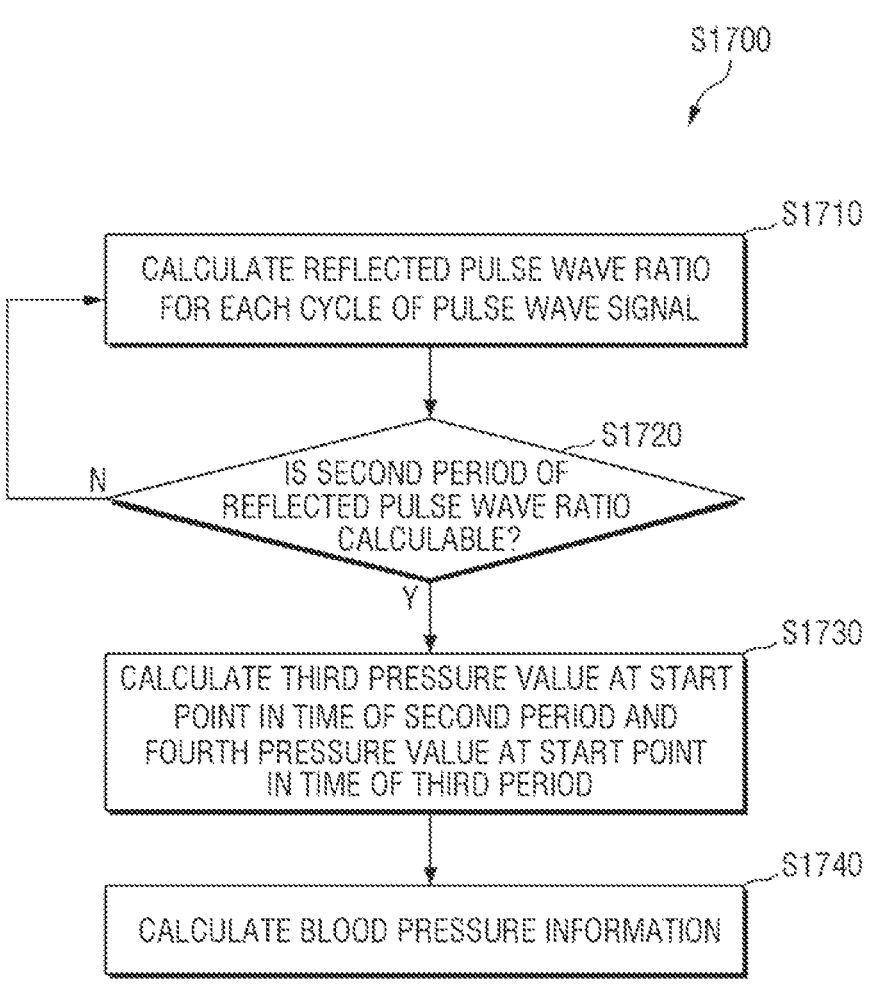
FIG. 29 is a flowchart illustrating a method of calculating a blood pressure using a generated pulse wave signal according to an embodiment of the present invention.
Figure 30:
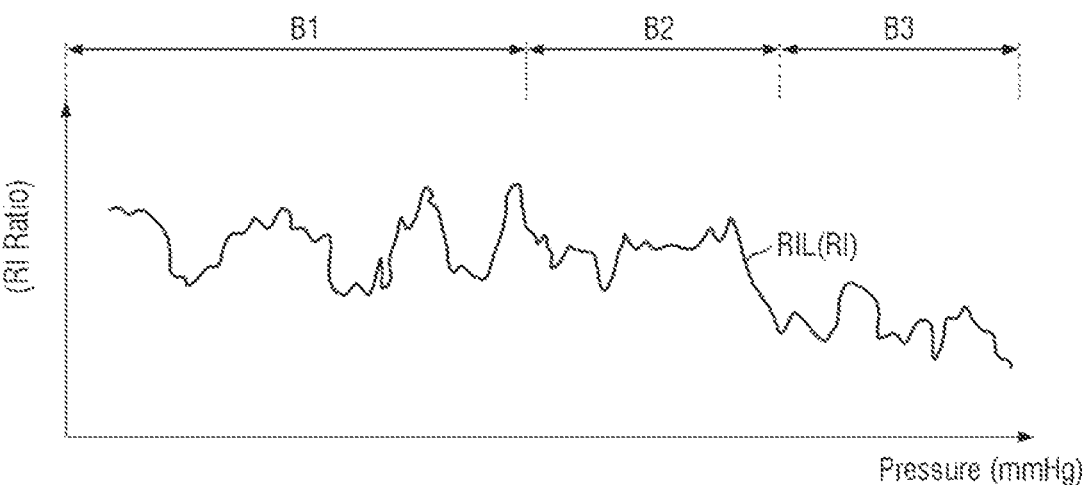
FIGS. 30 and 31 are graphs illustrating the method of calculating a blood pressure using a generated pulse wave signal according to an embodiment of the present invention.
Figure 31:
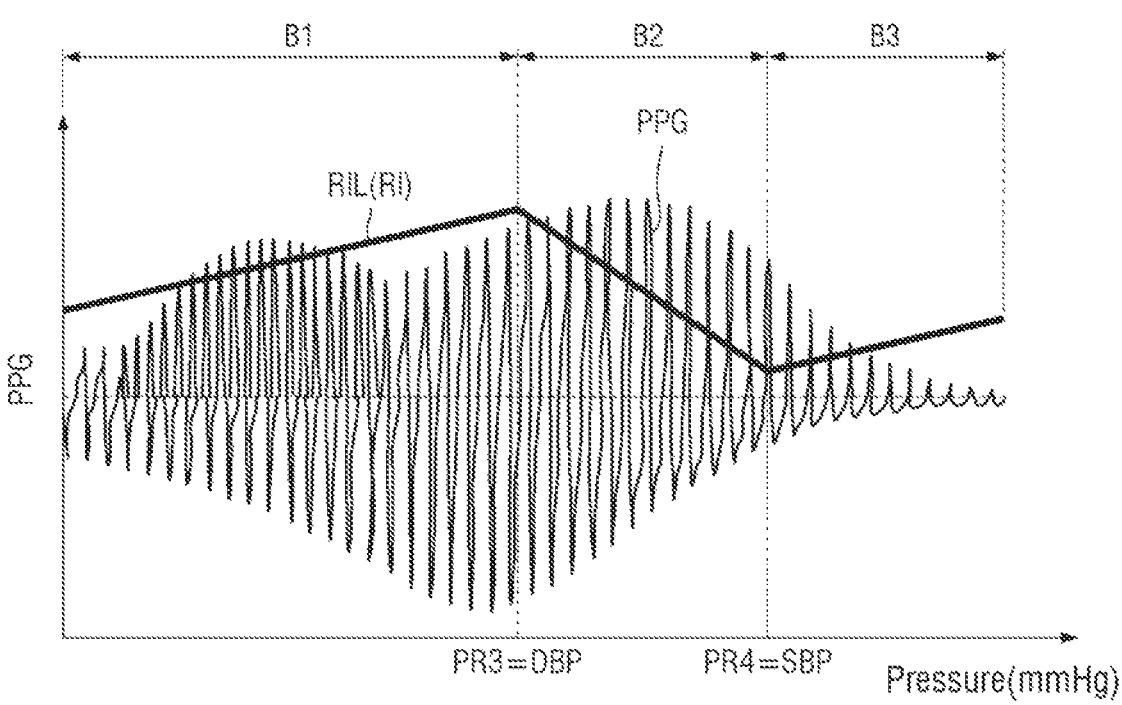

FIG. 22 is a flowchart illustrating a blood pressure measurement method using a display device according to an embodiment of the present invention. FIG. 23 is a flowchart illustrating a method of calculating a coefficient of a fourth transfer function according to an embodiment of the present invention. FIG. 24 is a graph illustrating a pulse wave frequency signal and a fourth transfer function according to an embodiment of the present invention. FIGS. 25 to 27 are enlarged graphs of waveforms of the pulse wave signal illustrated in FIG. 21. FIG. 28 is a flowchart illustrating a method of calculating a coefficient of a fourth transfer function according to an embodiment of the present invention. FIG. 29 is a flowchart illustrating a method of calculating a blood pressure using a generated pulse wave signal according to an embodiment of the present invention. FIGS. 30 and 31 are graphs illustrating the method of calculating a blood pressure using a generated pulse wave signal according to an embodiment of the present invention.

An embodiment of the present invention with reference to FIGS. 22 to 31 is substantially the same as an embodiment of the present invention with reference to FIGS. 7 to 21 except for a step of calculating a coefficient of a fourth transfer function and a step of calculating blood pressure information based on a second pulse wave signal, and a description thereof will thus be omitted to prevent redundant descriptions.

Referring to FIG. 22, first, the pressure sensing circuit 40 measures a pressure measurement value according to a pressure applying time, and the pulse wave sensing circuit 50 measures a pulse wave signal PPG value according to a pressure applying time (S1100). S1100 is substantially the same as S100 of FIG. 7, and a description thereof will thus be omitted to prevent redundant descriptions.

Next, the filter unit 800 generates the first pulse wave frequency signal FP1 that is converted into a magnitude of the pulse wave signal PPG according to a frequency having a fundamental wave component and a harmonics component based on the measurement values (S1200). S1200 is substantially the same as S200 of FIG. 7, and a description thereof will thus be omitted to prevent redundant descriptions.

Next, the filter unit 800 generates the second pulse wave frequency signal FP2 from which the $0^{th}$ harmonics f0 are removed by blocking noise of a fundamental wave component of the first pulse wave frequency signal FP1 (S1300). S1300 is substantially the same as S300 of FIG. 7, and a description thereof will thus be omitted to prevent redundant descriptions.

Next, the filter unit 800 generates the third pulse wave frequency signal FP3 from which the fourth harmonics f4 are removed by blocking a high-frequency noise component of the second pulse wave frequency signal FP2 (S1400). S1400 is substantially the same as S400 of FIG. 7, and a description thereof will thus be omitted to prevent redundant descriptions.

Next, a coefficient of a fourth transfer function H4(x) is calculated based on center frequencies and maximum gains of the first harmonics f1 to the third harmonics f3 of the third pulse wave frequency signal FP3 (S1500).

Referring further to FIGS. 23 and 24, first, the third pass filter 840 detects the first center frequency w01 and the first maximum gain k1 of the first harmonics f1 of the third pulse wave frequency signal FP3 (S1510). Next, the third pass filter 840 detects the second center frequency w02 of the second harmonics f2 of the third pulse wave frequency signal FP3 (S1520).

The third pass filter 840 may receive the third pulse wave frequency signal FP3 from the second pass filter 830. The third pass filter 840 may detect the center frequencies and the maximum gains in the first harmonics f1 to the third harmonics f3 of the third pulse wave frequency signal FP3. For example, the third pass filter 840 may detect the first center frequency w01 and the first maximum gain k1 of the first harmonics f1. In addition, the third pass filter 840 may also detect the second center frequency w02 of the second harmonics f2.

Third, the third pass filter 840 calculates a coefficient of the fourth transfer function H4(x) in a section from the first center frequency w01 to the second center frequency w02 (S1530).

The fourth transfer function H4(x) may have a form of a linear function. For example, the fourth transfer function H4(x) may have a waveform having a straight line form. When the fourth transfer function H4(x) has the form of the linear function, a second maximum gain k2 at the second center frequency w02 of the fourth transfer function H4(x) may be a half of the first maximum gain k1 at the first center frequency w01. In addition, the fourth transfer function H4(x) may have a gain corresponding to a first maximum gain k1 value at the first center frequency w01. That is, the fourth transfer function H4(x) may be calculated by Equation 3.

$$H4(x) = \frac{k}{2(w_{01} - w_{02})}x + \frac{k(w_{01} - 2w_{02})}{2(w_{01} - w_{02})} \qquad \text{[Equation 3]}$$

Here, W01 is the first center frequency, W02 is the second center frequency, k is the first maximum gain k1, x is an input pulse wave frequency signal, and H4(x) is the fourth transfer function.

In a case of the embodiment, the third pass filter 840 may change gains of the first harmonics f1 and the second harmonics f2 of the third pulse wave frequency signal FP3. Accordingly, the filter unit 800 may generate the second pulse wave signal PPG2, and the main processor 710 may calculate a reflected pulse wave ratio RI based on the second pulse wave signal PPG2. In this case, the reflected pulse wave ratio RI of the second pulse wave signal PPG2 may be changed by the third pass filter 840.

Referring to FIGS. 25 to 27, the main processor 710 may calculate the reflected pulse wave ratio RI of the pulse wave signal PPG. To calculate the reflected pulse wave ratio RI, the main processor 710 divides a wave cycle of the pulse wave signal PPG according to a period in which a wave according to a heartbeat and a reflected wave of a blood vessel are sequentially generated. For example, one cycle of the pulse wave signal PPG may include a plurality of waveforms having different amplitudes from each other. Accordingly, a peak value Sp of a waveform having the greatest amplitude among the plurality of waveforms may be a pulse wave contraction value, and a peak value Rp of a waveform having the second greatest amplitude among the plurality of waveforms may be a reflected pulse wave value. The pulse wave contraction value may be referred to as Sp. The reflected pulse wave value may be referred to as Rp, and the reflected pulse wave ratio RI may be referred to as RI. The reflected pulse wave ratio RI may be calculated by Equation 4.

$$RI = Rp/Sp \qquad \text{[Equation 4]}$$

Here, when the pulse wave signal PPG is inaccurate, the reflected pulse wave ratio RI may have a value of 1 or more, and when the pulse wave signal PPG is ideal, the reflected pulse wave ratio RI may have a value of 1 or less.

The third pass filter 840 may change the reflected pulse wave ratio RI of the second pulse wave signal PPG2 so as to accurately calculate blood pressure information. For example, FIG. 26 is a graph illustrating a third pulse wave signal PPG3 cycle and a fourth pulse wave signal PPG4 cycle according to the third pulse wave frequency signal FP3. FIG. 26 illustrates an example in which reflected pulse wave values R21 and R22 are detected to be greater than pulse wave contraction values S21 and S22 in the third pulse wave signal PPG3 cycle and the fourth pulse wave signal PPG4 cycle. That is, reflected pulse wave ratios RI of the third pulse wave signal PPG3 cycle and the fourth pulse wave signal PPG4 cycle are 1 or more. On the other hand, as in a case of FIG. 27, when the third pass filter 840 generates the second pulse wave signal PPG2 by changing the reflected pulse wave ratio RI, a reflected pulse wave ratio RI of a second pulse wave signal PPG2 cycle is 1 or less.

In summary, in a case of the embodiment, when the reflected pulse wave ratio RI of the second pulse wave signal PPG2 is greater than 1, the third pass filter 840 may change the reflected pulse wave ratio RI so that the reflected pulse wave ratio RI is greater than 1. Accordingly, noise components for each user are blocked, and thus, accuracy of blood pressure calculation based on the reflected pulse wave ratio RI may be improved.

Referring to FIG. 28, first, the third pass filter 840 detects the second center frequency w02 and the second maximum gain k2 of the second harmonics f2 of the third pulse wave frequency signal FP3 (S1511). Next, the third pass filter 840 detects the third center frequency w03 of the third harmonics f3 of the third pulse wave frequency signal FP3 (S1521). S1511 and S1521 are substantially the same as S1510 and S1520, respectively, of FIG. 23, and a description thereof will thus be omitted to prevent redundant descriptions.

Third, the third pass filter 840 calculates a coefficient of a fifth transfer function H5(x) in a section from the second center frequency w02 to the third center frequency w03 (S1531).

The fifth transfer function H5(x) may have a form of a linear function. For example, the fifth transfer function H5(x) may have a waveform having a straight line form. When the fifth transfer function H5(x) has the form of the linear function, a third maximum gain k3 at the third center frequency w03 of the fifth transfer function H5(x) may be a half of the second maximum gain k2 at the second center frequency w02. In addition, the fifth transfer function H5(x) may have a gain corresponding to a second maximum gain k2 value at the second center frequency w02. That is, the fifth transfer function H5(x) may be calculated by Equation 5.

$$H5(x) = \frac{k}{2(w_{02} - w_{03})}x + \frac{k(w_{02} - 2w_{03})}{2(w_{02} - w_{03})} \qquad \text{[Equation 5]}$$

Here, $W_{02}$ is the second center frequency, $W_{03}$ is the third center frequency, k is the second maximum gain k2, x is an input pulse wave frequency signal, and H5(x) is the fifth transfer function.

Finally, blood pressure information is calculated based on the second pulse wave signal (S1700).

Referring further to FIGS. 29 to 31, first, a reflected pulse wave ratio RI is calculated for each cycle of the pulse wave signal PPG (S1710). The reflected pulse wave ratio RI is substantially the same as the reflected pulse wave ratio RI of FIGS. 25 to 27, and a description thereof will thus be omitted to prevent redundant descriptions.

Second, the main processor 710 determines whether or not a second period B2 of the reflected pulse wave ratio RI may be calculated (S1720).

The main processor 710 sequentially stores detection results of reflected pulse wave ratios RI of reflected pulse waves to pulse wave contraction values, and analyzes the stored reflected pulse wave ratios RI. The main processor 710 may continuously make changes in magnitude of the reflected pulse wave ratios RI data to analyze a change in magnitude of reflected pulse wave ratio data RIL(RI).

The reflected pulse wave ratio RI includes a first period B1, in which the reflected pulse wave ratio RI fluctuates within a first range, a second period B2, in which the reflected pulse wave ratio RI fluctuates within a second range, and a third period B3, in which the reflected pulse wave ratio RI fluctuates within a third range. For example, the main processor 710 may analyze a reflected pulse wave ratio signal RIL to analyze a first period B1, the second period B2, the third period B3 and the like. In the first period B1, the reflected pulse wave ratio RI is changed within a preset range in a saturated state. For example, in the first period B1, the reflected pulse wave ratio RI may be gently changed within a preset range in a saturated state. In the second period B2, the reflected pulse wave ratio RI is decreased or increased in a preset range within a preset period. For example, in the second period B2, the reflected pulse wave ratio RI may be sharply decreased or increased in a preset range within a preset period. In the third period B3, the reflected pulse wave ratio RI is changed within a preset range in a saturated state again after it is decreased or increased. For example, in the third period B3, the reflected pulse wave ratio RI may be gently changed within a preset range in a saturated state again after it is sharply decreased or increased.

Here, each of a width of the first range and a width of the third range may be smaller than a width of the second range. For example, a combined width of the first range and a width of the third range may be smaller than a width of the second range. In addition, a gradient of the second period B2 of the reflected pulse wave ratio RI may be greater than a gradient of the first period B1 of the reflected pulse wave ratio RI and a gradient of the third period B3 of the reflected pulse wave ratio RI, individually or combined.

Finally, the main processor 710 calculates a systolic blood pressure SBP, a diastolic blood pressure DBP, and the like, based on the reflected pulse wave ratio RI (S1730), and calculates blood pressure information (S1740).

The main processor 710 may analyze the reflected pulse wave ratio RI to detect a start point in time of the second period B2. In addition, the main processor 710 may calculate a third pressure value PR3 corresponding to the pulse wave signal PPG at the start point in time of the second period B2. In addition, the main processor 710 may calculate the third pressure value PR3 as the diastolic blood pressure DBP. In addition, the main processor 710 may analyze the reflected pulse wave ratio RI to detect a start point in time of the third period B3 after the second period B2. In addition, the main processor 710 may calculate a fourth pressure value PR4 corresponding to the pulse wave signal PPG at the start point in time of the third period B3. In addition, the main processor 710 may calculate the fourth pressure value PR4 as the systolic blood pressure SBP.

In a case of the embodiment, for example, FIG. 30 illustrates an example in which the reflected pulse wave ratio data RIL(RI) is inaccurately calculated. FIG. 31 illustrates an example in which the reflected pulse wave ratio data RIL(RI) is accurately calculated. In a case of FIG. 30, the first period B1 to the third period B3 of the reflected pulse wave ratio data RIL(RI) might not be analyzed. Accordingly, as in a case of FIG. 31, the third pass filter 840 may block noise for each user. For example, the third pass filter 840 may generate the second pulse wave signal PPG2 to accurately calculate the reflected pulse wave ratio data RIL(RI). Accordingly, noise components for each user are blocked, and thus, accuracy of blood pressure calculation based on the pulse wave ratio RI may be increased.

Embodiments of the present invention provide a display device capable of extracting and blocking noise components for each user, and a blood pressure measurement method using the same.

With a display device and a blood pressure measurement method using the same according to embodiments of the present invention, a blood pressure of a user may be measured by sensing light reflected from a blood vessel or the like of a finger of the user by a photo-sensor of a display panel and analyzing a pulse wave signal according to an amount of the sensed light.

For example, when blood pressure calculation is inaccurate due to the presence of different noise components for each user in the pulse wave signal, accuracy of the blood pressure calculation may be increased by extracting and blocking the noise components for each user.

While the present invention has been described with reference to the embodiments thereof, it will be understood by those of ordinary skill in the art that various changes in form and detail may be made thereto without departing from the spirit and scope of the present invention.

What is claimed is:

1. A blood pressure measurement method using a display device, comprising:

generating a first pulse wave frequency signal by a main processor included in the display device, the first pulse wave frequency signal having a magnitude of a pulse wave signal according to a frequency having a fundamental wave component and a harmonics component based on a pressure measurement value that is sensed by a pressure sensor disposed on a display panel included in the display device and sensing a pressure applied from outside of the display device and a pulse wave signal that is sensed by a photo-sensor disposed on the display panel and sensing light;

calculating a coefficient of a transfer function by the main processor, the coefficient of the transfer function is based on center frequencies and maximum gains at center frequencies of first harmonics to third harmonics of the first pulse wave frequency signal;

generating a second pulse wave frequency signal by the main processor, the second pulse wave frequency signal is generated by blocking noise components of the first harmonics to the third harmonics of the first pulse wave frequency signal based on the transfer function;

generating a first pulse wave signal by the main processor, the first pulse wave signal having a magnitude of a pulse wave signal according to a pressure based on the second pulse wave frequency signal; and calculating blood pressure information by the main processor based on the first pulse wave signal, wherein the blood pressure information is displayed on a display panel of the display device, wherein the calculating of the coefficient of the transfer function based on the center frequencies and the maximum gains at the center frequencies of the first harmonics to the third harmonics of the first pulse wave frequency signal includes:

detecting a first center frequency and a maximum gain at the first center frequency of the first harmonics of the first pulse wave frequency signal, a second center frequency and a maximum gain at the second center frequency of the second harmonics of the first pulse wave frequency signal, and a third center frequency and a maximum gain at the third center frequency of the third harmonics of the first pulse wave frequency signal; and calculating cutoff frequencies based on the center frequencies, wherein the calculating of the cutoff frequencies based on the center frequencies includes calculating a first cutoff frequency as corresponding to a half of the first center frequency, wherein the transfer function includes a first transfer function blocking a noise component of the first harmonics in a section from the first cutoff frequency to the first center frequency, wherein the first transfer function is calculated by $$H1(x) = \frac{k}{w_{01}^N - w_{c1}^N} x^N + \frac{-kw_{c1}^N}{w_{01}^N - w_{c1}^N}$$

in which $H1(x)$ is the first transfer function, $w_{o1}$ is the first center frequency, k is the maximum gain of the first center frequency, $w_{c1}$ is the first cutoff frequency, and N is a natural number of 2 or more.

2. The blood pressure measurement method using a display device of claim 1, wherein the first transfer function has a waveform of a convex polynomial function.

3. The blood pressure measurement method using a display device of claim 1, wherein the calculating of the cutoff frequencies based on the center frequencies further includes calculating a second cutoff frequency corresponding to an intermediate value between the first center frequency and the second center frequency.

4. The blood pressure measurement method using a display device of claim 3, wherein the transfer function includes a second transfer function blocking a noise component of the first harmonics in a section from the first center frequency to the second cutoff frequency, and the second transfer function is calculated by $$H2(x) = \frac{-k}{w_{c2}^N - w_{01}^N} x^N + \frac{-kw_{01}^N}{w_{c2}^N - w_{01}^N}$$

in which $H2(x)$ is the second transfer function, $w_{o1}$ is the first center frequency, k is the maximum gain of the first center frequency, wc2 is the second cutoff frequency, and N is a natural number of 2 or more.

5. The blood pressure measurement method using a display device of claim 4, wherein a maximum gain of the first transfer function is the same as a maximum gain of the second transfer function.

6. The blood pressure measurement method using a display device of claim 1, wherein in the calculating of the blood pressure information based on the first pulse wave signal, a peak detection signal is generated using peak values of the first pulse wave signal, a pressure value corresponding to the peak value of the peak detection signal is calculated, and a diastolic blood pressure lower than the pressure value, a systolic blood pressure higher than the pressure value, and a mean blood pressure are calculated according to the pressure value.

7. The blood pressure measurement method using a display device of claim 6, wherein a first pressure value and a second pressure value are calculated, wherein the first pressure value is smaller than the pressure value corresponding to about 60% to about 80% of the peak value in the peak detection signal, and the second pressure value is greater than the pressure value, and the first pressure value is calculated as the diastolic blood pressure, and the second pressure value is calculated as the systolic blood pressure.

8. The blood pressure measurement method using a display device of claim 1, further comprising generating a second pulse wave frequency signal by blocking noise of the fundamental wave component of the first pulse wave frequency signal.

9. The blood pressure measurement method using a display device of claim 8, wherein the fundamental wave component includes a signal having a frequency of 0 hz.

10. The blood pressure measurement method using a display device of claim 8, further comprising generating a third pulse wave frequency signal from which fourth harmonics greater than the third harmonics are removed by blocking a high-frequency noise component of the second pulse wave frequency signal.

11. A blood pressure measurement method using a display device, comprising:

generating a first pulse wave frequency signal by a main processor included in the display device, the first pulse wave frequency signal having a magnitude of a pulse wave signal according to a frequency having a fundamental wave component and a harmonics component based on a pressure measurement value that is sensed by a pressure sensor disposed on a display panel included in the display device and sensing a pressure applied from outside of the display device and a pulse wave signal that is sensed by a photo-sensor disposed on the display panel and sensing light;

calculating a coefficient of a transfer function by the main processor, the coefficient of the transfer function is based on center frequencies and maximum gains at center frequencies of first harmonics to third harmonics of the first pulse wave frequency signal;

generating a second pulse wave frequency signal by the main processor, the second pulse wave frequency signal is generated by changing the maximum gains of the first harmonics to the third harmonics of the first pulse wave frequency signal based on the transfer function;

generating a second pulse wave signal by the main processor, the second pulse wave signal having a magnitude of a pulse wave signal according to a pressure based on the second pulse wave frequency signal; and calculating blood pressure information by the main processor based on the second pulse wave signal and displaying the blood pressure information on a display panel of the display device, wherein one cycle of the second pulse wave signal includes a plurality of waveforms having different amplitudes from each other, and a peak value of a first waveform of the plurality of waveforms is greater than a peak value of a second waveform of the plurality of waveforms, wherein the calculating of the coefficient of the transfer function based on the center frequencies and the maximum gains at the center frequencies of the first harmonics to the third harmonics of the first pulse wave frequency signal includes:

calculating a first center frequency and a maximum gain at the first center frequency of the first harmonics of the first pulse wave frequency signal, a second center frequency and a maximum gain at the second center frequency of the second harmonics of the first pulse wave frequency signal, and a third center frequency and a maximum gain at the third center frequency of the third harmonics of the first pulse wave frequency signal; and calculating cutoff frequencies based on the center frequencies, wherein the calculating of the cutoff frequencies based on the center frequencies includes calculating a first cutoff frequency as corresponding to a half of the first center frequency, wherein the transfer function includes a first transfer function blocking a noise component of the first harmonics in a section from the first cutoff frequency to the first center frequency, wherein the first transfer function is calculated by $$H1(x) = \frac{k}{w_{01}^N - w_{c1}^N}x^N + \frac{-kw_{c1}^N}{w_{01}^N - w_{c1}^N}$$

in which $H1(x)$ is the first transfer function, $w_{o1}$ is the first center frequency, k is the maximum gain of the first center frequency, $w_{c1}$ is the first cutoff frequency, and N is a natural number of 2 or more.

12. The blood pressure measurement method using a display device of claim 11, wherein the transfer function includes a third transfer function in which the peak value of the first waveform is greater than the peak value of the second waveform, and the third transfer function is calculated by $$H3(x) = \frac{k}{2(w_{01} - w_{02})}x + \frac{k(w_{01} - 2w_{02})}{2(w_{01} - w_{02})}$$

in which $w_{o1}$ is the first center frequency, k is a maximum gain of the first center frequency, and $w_{o2}$ the second center frequency.

13. The blood pressure measurement method using a display device of claim 12, wherein RI=Rp/Sp in which RI is a reflected pulse wave ratio, Sp is a pulse wave contraction value, Rp is a reflected pulse wave value, wherein the pulse wave contraction value is the peak value of the first waveform of the plurality of waveforms, and the reflected pulse wave value is the peak value of the second waveform of the plurality of waveforms.

14. The blood pressure measurement method using a display device of claim 13, wherein the reflected pulse wave ratio includes a first period in which the reflected pulse wave ratio fluctuates within a first range, a second period in which the reflected pulse wave ratio fluctuates within a second range, and a third period in which the reflected pulse wave ratio fluctuates within a third range, and wherein a width of the first range and a width of the third range are smaller than a width of the second range.

15. The blood pressure measurement method using a display device of claim 14, wherein the reflected pulse wave ratio is analyzed to detect a start point in time of the second period, wherein a third pressure value corresponding to the second pulse wave signal at the start point in time of the second period is calculated and set as a diastolic blood pressure, and wherein a fourth pressure value corresponding to the second pulse wave signal at a start point in time of the third period after the second period is calculated and set as a systolic blood pressure.

16. An electronic device, comprising:

a display device comprising:

a display panel including pixels displaying an image;

a pressure sensor disposed on the display panel and sensing a pressure applied from outside of the display device;

a photo-sensor disposed on the display panel and sensing light; and a main processor receiving a pressure measurement value that is sensed by the pressure sensor and a pulse wave signal that is sensed by the photo-sensor, wherein the main processor generates a first pulse wave frequency signal having a fundamental wave component and a harmonics component according to the pressure measurement value and the pulse wave signal, generates a second pulse wave frequency signal by blocking noise of the harmonics component of the first pulse wave frequency signal, generates a first pulse wave signal based on the second pulse wave frequency signal, and calculates blood pressure information based on the first pulse wave signal, wherein each of the first pulse wave frequency signal and the second pulse wave frequency signal is a magnitude of the pulse wave signal according to a frequency, and the first pulse wave signal is a magnitude of the pulse wave signal according to the pressure measurement value, wherein the main processor calculates a coefficient of a transfer function based on center frequencies and maximum gains at center frequencies of first harmonics to third harmonics of the first pulse wave frequency signal, wherein the calculating of the coefficient of the transfer function based on the center frequencies and the maximum gains at the center frequencies of the first harmonics to the third harmonics of the first pulse wave frequency signal includes:

detecting a first center frequency and a maximum gain at the first center frequency of the first harmonics of the first pulse wave frequency signal, a second center frequency and a maximum gain at the second center frequency of the second harmonics of the first pulse wave frequency signal, and a third center frequency and a maximum gain at the third center frequency of the third harmonics of the first pulse wave frequency signal; and calculating cutoff frequencies based on the center frequencies, wherein the calculating of the cutoff frequencies based on the center frequencies includes calculating a first cutoff frequency as corresponding to a half of the first center frequency, wherein the transfer function includes a first transfer function blocking a noise component of the first harmonics in a section from the first cutoff frequency to the first center frequency, wherein the first transfer function is calculated by $$H1(x) = \frac{k}{w_{01}^N - w_{c1}^N} x^N + \frac{-kw_{c1}^N}{w_{01}^N - w_{c1}^N}$$

in which $H1(x)$ is the first transfer function, war is the first center frequency, $k$ is the maximum gain of the first center frequency, $w_{c1}$ is the first cutoff frequency, and $N$ is a natural number of 2 or more.

* * * * *